United States Patent
Asbun et al.

(10) Patent No.: US 11,250,263 B2
(45) Date of Patent: Feb. 15, 2022

(54) GAZE-DRIVEN AUGMENTED REALITY

(71) Applicant: InterDigital Patent Holdings, Inc., Wilmington, DE (US)

(72) Inventors: Eduardo Asbun, San Diego, CA (US); Yuriy Reznik, Seattle, WA (US); Ariela Zeira, Huntington, NY (US); Gregory S. Sternberg, Mt. Laurel, NJ (US); Ralph Neff, San Diego, CA (US)

(73) Assignee: InterDigital Patent Holdings, Inc., Wilmington, DE (US)

( * ) Notice: Subject to any disclaimer, the term of this patent is extended or adjusted under 35 U.S.C. 154(b) by 0 days.

(21) Appl. No.: 15/924,956

(22) Filed: Mar. 19, 2018

(65) Prior Publication Data
US 2018/0211112 A1 Jul. 26, 2018

Related U.S. Application Data

(63) Continuation of application No. 15/028,233, filed as application No. PCT/US2014/060016 on Oct. 10, 2014, now Pat. No. 9,922,253.
(Continued)

(51) Int. Cl.
*A61B 5/00* (2006.01)
*A61B 5/0476* (2006.01)
(Continued)

(52) U.S. Cl.
CPC ........ *G06K 9/00671* (2013.01); *A61B 5/0022* (2013.01); *A61B 5/1112* (2013.01);
(Continued)

(58) Field of Classification Search
CPC ...... H04W 4/30; A61B 5/0022; A61B 5/1112; A61B 5/165; A61B 5/742; A61B 3/113;
(Continued)

(56) References Cited

U.S. PATENT DOCUMENTS

| | | | |
|---|---|---|---|
| 2001/0051160 A1* | 12/2001 | Jacobs | A61K 36/258 424/190.1 |
| 2004/0210159 A1* | 10/2004 | Kibar | A61B 5/4803 600/558 |

(Continued)

FOREIGN PATENT DOCUMENTS

| | | |
|---|---|---|
| CN | 102076387 A | 5/2011 |
| CN | 103561635 A | 2/2014 |

(Continued)

OTHER PUBLICATIONS

Wayback Machine Google, "Google Glass", Product web page: http://www.google.com/glass , dated May 1, 2013, 1 page.
(Continued)

*Primary Examiner* — Jin Cheng Wang
(74) *Attorney, Agent, or Firm* — Condo Roccia Koptiw LLP

(57) ABSTRACT

Augmented reality (AR) systems, methods, and instrumentalities are disclosed. A user's gaze point may be estimated and may be used to search for and present information, e.g., information relating to areas on which the user is focusing. The user's gaze point may be used to facilitate or enable modes of interactivity and/or user interfaces that may be controlled by the direction of view of the user. Biometric techniques may be used to estimate an emotional state of the user. This estimated emotional state may be used to be the information that is presented to the user.

21 Claims, 22 Drawing Sheets

Related U.S. Application Data

(60) Provisional application No. 61/889,900, filed on Oct. 11, 2013.

(51) Int. Cl.
| | |
|---|---|
| *A61B 5/053* | (2021.01) |
| *A61B 5/11* | (2006.01) |
| *A61B 5/16* | (2006.01) |
| *G02B 27/01* | (2006.01) |
| *G06K 9/00* | (2006.01) |
| *G06F 3/01* | (2006.01) |
| *H04W 4/30* | (2018.01) |
| *G16H 40/67* | (2018.01) |
| *A61B 5/0533* | (2021.01) |
| *A61B 5/369* | (2021.01) |

(52) U.S. Cl.
CPC .............. *A61B 5/165* (2013.01); *A61B 5/742* (2013.01); *G02B 27/017* (2013.01); *G06F 3/013* (2013.01); *G06K 9/00302* (2013.01); *G06K 9/00604* (2013.01); *G16H 40/67* (2018.01); *H04W 4/30* (2018.02); *A61B 5/0533* (2013.01); *A61B 5/369* (2021.01); *G06F 3/015* (2013.01)

(58) Field of Classification Search
CPC .. G02B 27/017; G06F 3/013; G06K 9/00302; G06K 9/00604; G06K 9/00671; G06Q 30/02
USPC ......................................................... 345/633
See application file for complete search history.

(56) References Cited

U.S. PATENT DOCUMENTS

| | | | | |
|---|---|---|---|---|
| 2006/0009702 | A1 | 1/2006 | Iwaki et al. | |
| 2008/0312796 | A1* | 12/2008 | Matsuura | B60N 2/0248 701/49 |
| 2009/0167787 | A1* | 7/2009 | Bathiche | A63F 13/10 345/633 |
| 2009/0270170 | A1 | 10/2009 | Patton | |
| 2010/0131291 | A1* | 5/2010 | Firminger | G06Q 10/04 705/3 |
| 2010/0131602 | A1* | 5/2010 | Firminger | G06F 19/00 709/206 |
| 2010/0226535 | A1 | 9/2010 | Kimchi et al. | |
| 2011/0085700 | A1* | 4/2011 | Lee | G06Q 30/02 382/103 |
| 2011/0134026 | A1* | 6/2011 | Kang | G06F 3/011 345/156 |
| 2011/0137137 | A1 | 6/2011 | Shin et al. | |
| 2012/0004575 | A1* | 1/2012 | Thorn | G06F 16/48 600/587 |
| 2012/0062595 | A1 | 3/2012 | Oh et al. | |
| 2012/0098859 | A1* | 4/2012 | Lee | G06K 9/00671 345/633 |
| 2012/0290401 | A1* | 11/2012 | Neven | A61B 3/113 705/14.68 |
| 2012/0308972 | A1* | 12/2012 | Miller | G06F 3/048 434/236 |
| 2013/0147837 | A1* | 6/2013 | Stroila | G06T 11/60 345/633 |
| 2013/0147838 | A1 | 6/2013 | Small et al. | |
| 2013/0204535 | A1* | 8/2013 | Kapoor | G16H 50/50 702/19 |
| 2014/0049546 | A1* | 2/2014 | Wang | G06T 11/20 345/441 |
| 2014/0098126 | A1* | 4/2014 | Fein | G06T 11/00 345/633 |
| 2014/0098137 | A1* | 4/2014 | Fein | G06T 11/60 345/633 |
| 2014/0139551 | A1* | 5/2014 | McCulloch | G09G 5/377 345/633 |
| 2014/0225915 | A1* | 8/2014 | Theimer | G02B 27/017 345/633 |
| 2014/0225918 | A1 | 8/2014 | Mittal et al. | |
| 2014/0280296 | A1* | 9/2014 | Johnston | G06F 17/30011 707/769 |
| 2015/0063665 | A1* | 3/2015 | Sasakido | G06K 9/00671 382/128 |
| 2019/0228639 | A1* | 7/2019 | Hosoda | G06K 9/00664 |
| 2019/0252063 | A1* | 8/2019 | Gordon | G16H 10/60 |

FOREIGN PATENT DOCUMENTS

| | | |
|---|---|---|
| EP | 2428915 A2 | 3/2012 |
| JP | 2005-315802 A | 11/2005 |
| WO | WO 2012/154418 A1 | 11/2012 |

OTHER PUBLICATIONS

Girod et al., "Mobile Visual Search: Architectures, Technologies, and the Emerging MPEG Standard", IEEE MultiMedia, vol. 18, No. 3, Aug. 15, 2011, pp. 86-94.

Girod et al., "Mobile Visual Search", IEEE Signal Processing Magazine, vol. 28, No. 4, Jul. 2011, pp. 61-76.

Lemahieu et al., "Low Cost Eye Tracking for Human-Machine Interfacing", Journal of Eye Tracking, Visual Cognition and Emotion, vol. 1, No. 1, May 31, 2011, 12 pages.

Perez et al., "A Precise Eye-Gaze Detection and Tracking System", The Proceedings of 11th International Conference in Central Europe on Computer Graphics, Visualization and Computer Vision, Feb. 3-7, 2003, pp. 105-108.

Takacs et al., "Outdoors Augmented Reality on Mobile Phone using Loxel-Based Visual Feature Organization", Proceedings of the 1st ACM International Conference on Multimedia Information Retrieval, Vancouver, British Columbia, Canada, Oct. 30-31, 2008, pp. 427-434.

Talmi et al., "Eye and Gaze Tracking for Visually Controlled Interactive Stereoscopic Displays", Signal Processing: Image Communication, vol. 14, No. 10, Aug. 1999, 9 pages.

Time Magzine, "Google Glass", Best Inventions of the Year 2012, Available at http://techland.time.com/2012/11/01/best-inventions-of-the-year-2012/slide/google-glass/, Oct. 31, 2012, 2 pages.

* cited by examiner

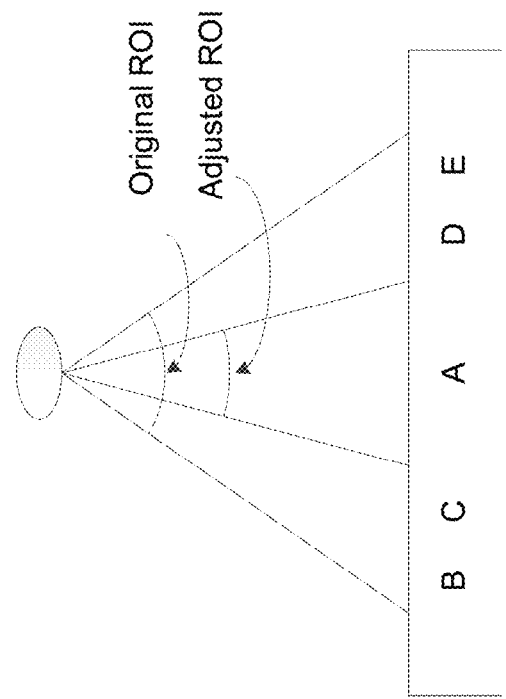
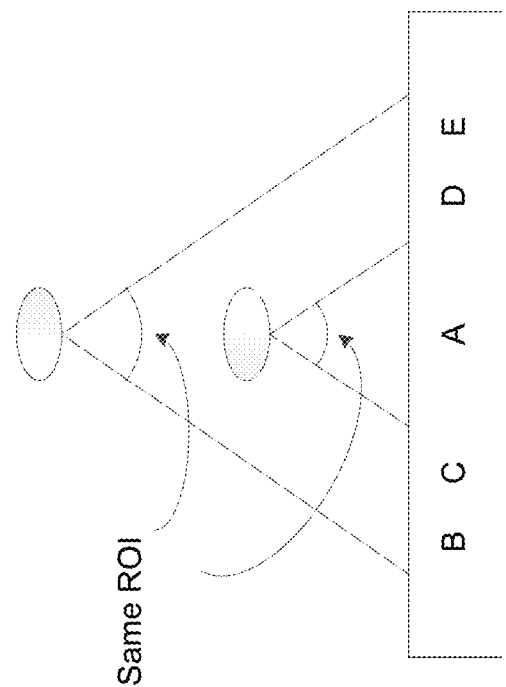
FIG. 11A
FIG. 11B

GAZE-DRIVEN AUGMENTED REALITY

CROSS-REFERENCE TO RELATED APPLICATIONS

This application is a continuation application of U.S. Ser. No. 15/028,233, filed Apr. 8, 2016, which is the National Stage Entry under 35 U.S.C. § 371 of Patent Cooperation Treaty Application No. PCT/US2014/060016, filed Oct. 10, 2014, which claims the benefit of U.S. Provisional Application No. 61/889,900, filed Oct. 11, 2013, the disclosures of which are incorporated herein by reference in their entireties.

BACKGROUND

In augmented reality (AR), a user's view of the real world may be digitally enhanced (or augmented) by adding a layer, or layers, of digital information on top of an image being viewed through a device (such as a smartphone, tablet, or wearable electronic device (such as the GOOGLE GLASS® system)). Some applications of AR may include sightseeing (e.g., providing information on nearby businesses or attractions), gaming (e.g., digital game play in a real world environment), navigation, and others.

Applications of AR may be suitable for wireless transmit/receive units (WTRUs), such as mobile devices, because mobile devices may be equipped with cameras, sensors, a global positioning system (GPS), and a gyroscope (such as to determine the direction of the camera view). A WTRU also has send/receive capabilities to interact with a server.

SUMMARY

Augmented reality (AR) systems, methods, and instrumentalities are disclosed. A user's gaze point may be estimated and may be used to search for and present information, e.g., only present information relating to areas to which the user is focusing his or her direction of view. The user's gaze point may be used to facilitate or enable modes of interactivity and/or user interfaces that may be controlled by the direction of view of the user.

Biometric techniques may be used to estimate an emotional state of the user. This estimated emotional state may be used to refine the information that is presented to the user.

A method of presenting information in an AR system may involve determining a gaze point of a user and a region of interest (ROI) as a function of the gaze point. Information pertaining to an object in the ROI may be presented. An emotional state of a user may be determined as a function of biometric data pertaining to the user. The search result may be filtered as a function of the determined emotional state.

BRIEF DESCRIPTION OF THE DRAWINGS

FIG. 11A is a diagram illustrating different results from a ROI resulting from differing distances to a target.

FIG. 11B is a diagram illustrating adjustment of a size of a ROI.

DETAILED DESCRIPTION

A detailed description of illustrative embodiments will now be described with reference to the various Figures. Although this description provides a detailed example of possible implementations, it should be noted that the details are intended to be exemplary and in no way limit the scope of the application.

Figure 1:
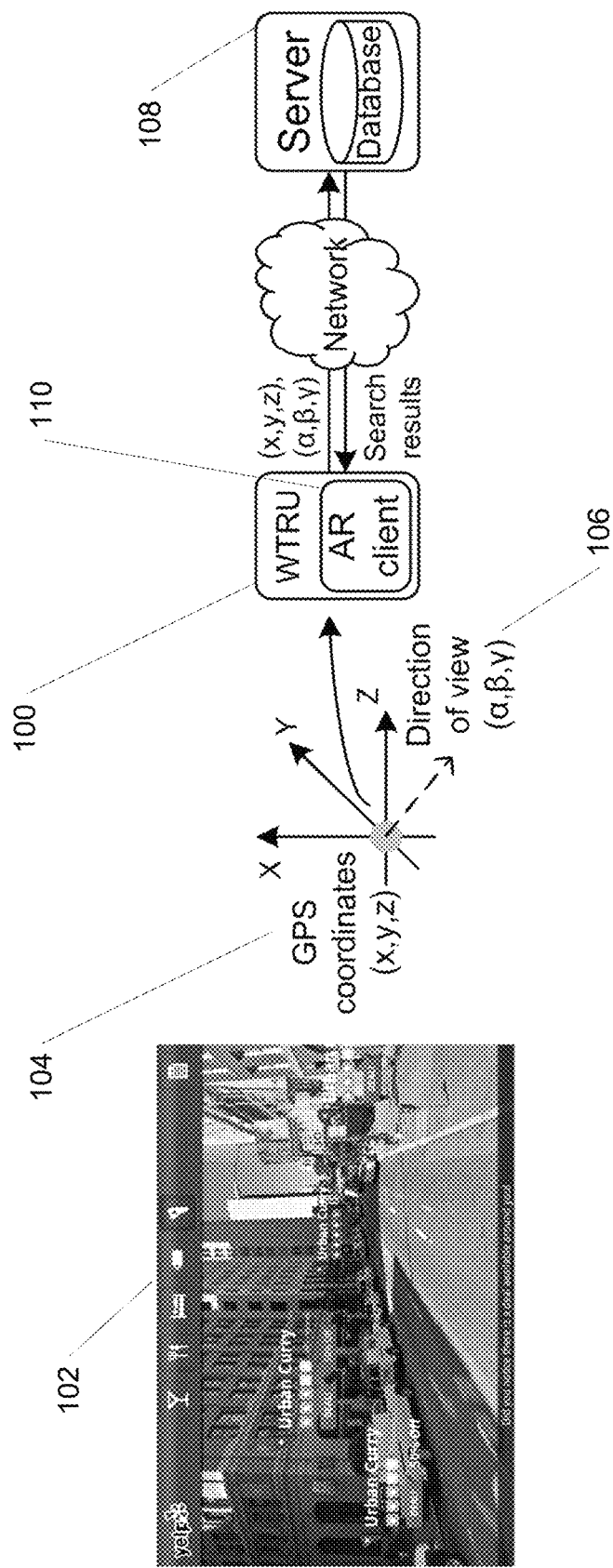
FIG. 1 is a diagram illustrating example elements of an augmented reality (AR) system.

FIG. 1 illustrates example elements of an augmented reality (AR) system including a mobile device, such as a WTRU 100. User experience in an AR system may be enhanced by presenting information that may be relevant to the user. By estimating a user's direction of view, a search space may be characterized, e.g., limited. The quality of results may be improved, and the usage of processing and network resources may be reduced. A user's gaze point may be estimated and may be used to search for and present information, e.g., only present information relating to areas to which the user is focusing his or her direction of view. The user's gaze point may be used to facilitate or enable modes of interactivity and/or user interfaces that may be controlled by the direction of view of the user. Biometric techniques may be used to estimate an emotional state of the user. This estimated emotional state may be used to refine the information that is presented to the user.

A camera may be used to capture an image 102 or video of a scene. GPS may be used to determine a geographical location, e.g., GPS coordinates 104, of the mobile device, and a gyroscope may be used to determine a direction of the camera view 106. This information may be sent to a server 108, which may determine whether the WTRU 100 is located close to objects of interest and whether they are within the field of view of the camera. The results may be provided to an AR client 110, and the AR client 110 may highlight these objects by superimposing text or images on the device's display.

In location-based AR, relevant information may be selected based on the user's geolocation (e.g., obtained using GPS or wireless networks) and/or orientation information (e.g., obtained using gyroscope or compass). This type of AR may be used with mapping or navigation applications, where users may want to find stores or services near their location.

Figure 2A:
FIG. 2A is a diagram illustrating example AR information superimposed on an image.
Figure 2B:
FIG. 2B is a diagram illustrating an example of incorrectness or inconsistency of AR information superimposed on an image.

FIG. 2A illustrates that results may be superimposed on preexisting images or video, or may be overlaid on images or video captured using a camera. An advantage of this technique is that relatively little information may be sent to and received from the server; therefore, the communication overhead may be reduced and the response time may be improved. However, the geolocation and/or orientation information may be inaccurate, the view of the camera may be blocked, and/or the camera may be pointing to an unrelated object. These conditions may result in incorrect or inconsistent information being shown to the user, as in FIG. 2B, in which the view of the camera may have little or no relation to the information overlaid on the screen.

Figure 3:
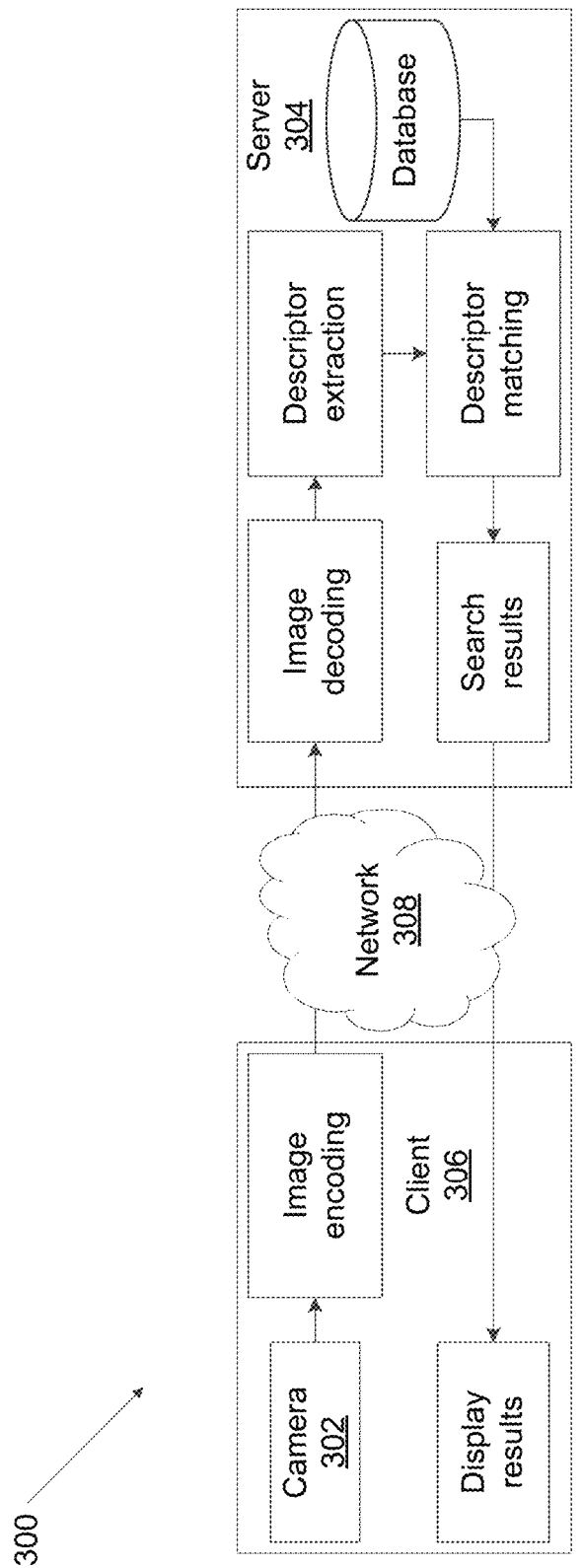
FIG. 3 is a block diagram illustrating an example system for implementing an AR technique.

FIG. 3 depicts an example system 300 that may implement an AR technique that may use an image or images captured by a camera 302, e.g., in real-time to perform a visual search about objects in the user's visual proximity. A visual search may be performed by a server 304, e.g., entirely by the server 304. For example, an image or images may be sent by a client 306 to the server 304, which may perform the search. Results may then be sent back to the client 306 for display by the client 306. This approach may offload most of the processing to the server 304, but may involve transmission of a possibly large amount of information over a network 308, which may increase latency.

Figure 4:
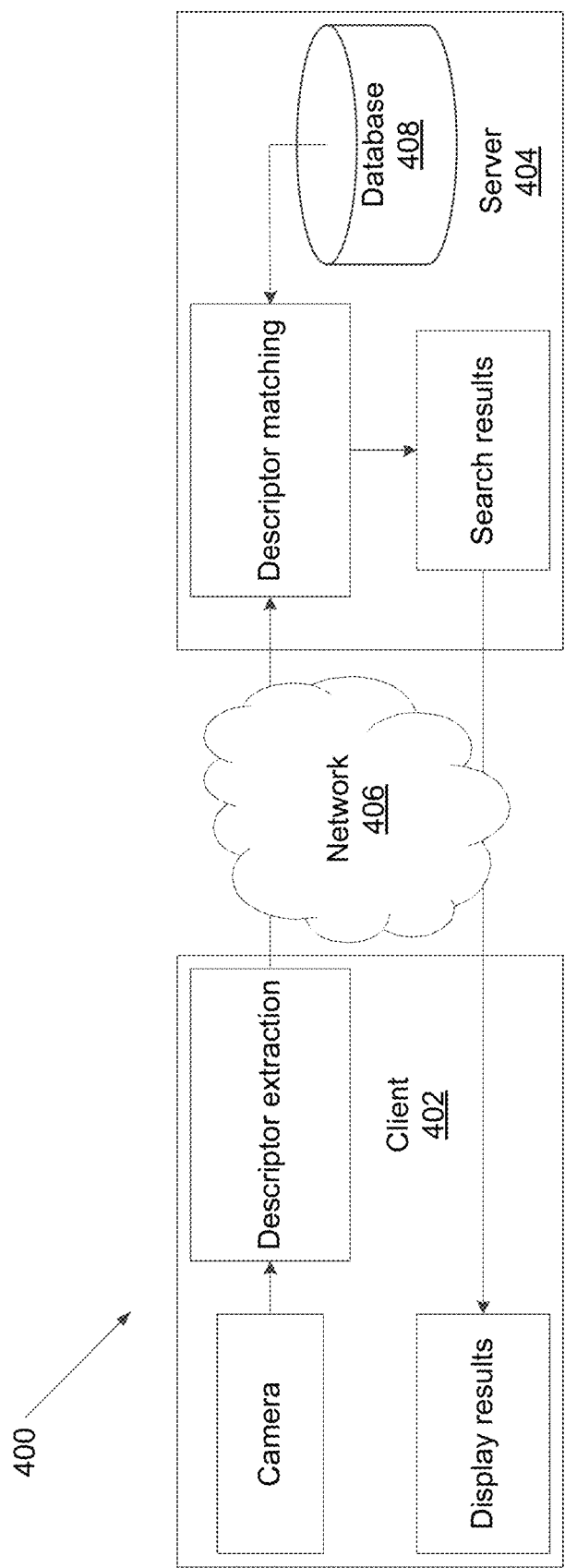
FIG. 4 is a block diagram illustrating another example system for implementing an AR technique.

FIG. 4 depicts an example system 400 that may implement an AR technique in which part of the processing may be done by a client 402 (e.g., a "client-server" model). The client 402 may extract relevant features from the captured image(s) to obtain a set of descriptors that are used by a server 404 to perform the search. With this approach, the amount of information sent over a network 406 may be significantly reduced, improving the system response time. However, processing requirements at the client 402 may increase. If client capability is high, a subset of a database 408 may be cached at the client 402 to further improve system performance.

Users may capture image or video under a variety of conditions, e.g., lighting, occlusion, camera tilt, etc. Improving the robustness of the system may improve performance under these conditions. In addition, reducing search latency may improve real-time operation. To improve the performance of visual search, a visual search may be conducted on a subset of data available at the server. For example, irrelevant data may be limited, e.g., by considering locations that are close to the user's position.

Information presented to the user may correspond to the view being shown on the device's display, thus increasing its relevance. However, for client-server models, processing time may be spent on descriptor extraction for objects that are of no interest to the user. Further, for server-centric systems, query images may be sent from clients to a remote server. This may create a significant amount of network traffic.

Other issues may be related to the user interface. For example, a search may result in a large number of matching objects, potentially complicating on-screen annotations.

Figure 5:
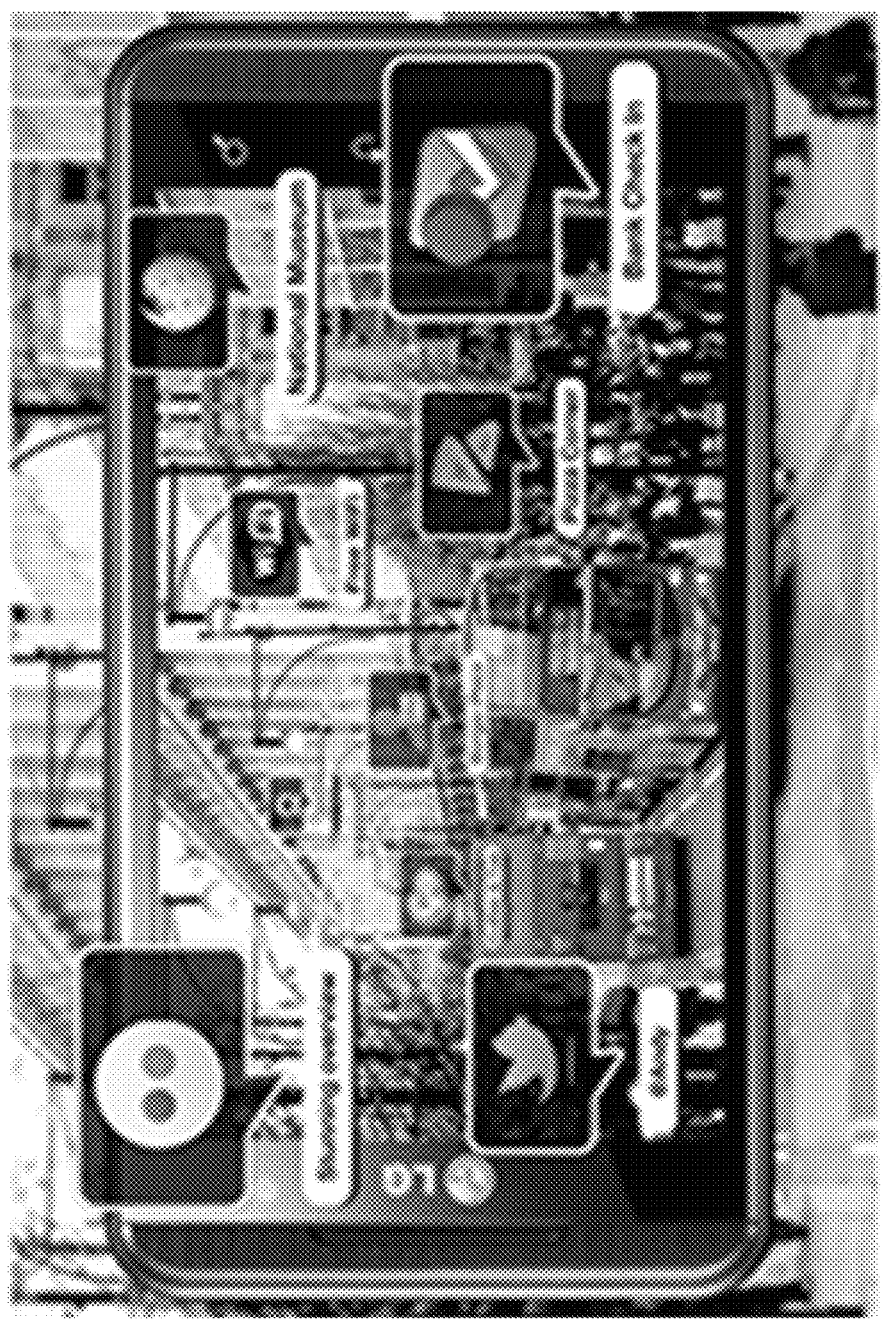
FIG. 5 is a diagram illustrating an example AR search result.

FIG. 5 illustrates an example screenshot 502. The system may find it difficult or impossible to reduce the number of displayed objects if it has no way of knowing which of the displayed objects are important to the user. Some users may experience information overload as they may be presented with results that may not be relevant to them. In addition, with small screens or if annotations are overlapping, selecting a particular result from multiple results may be challenging.

Figure 6:
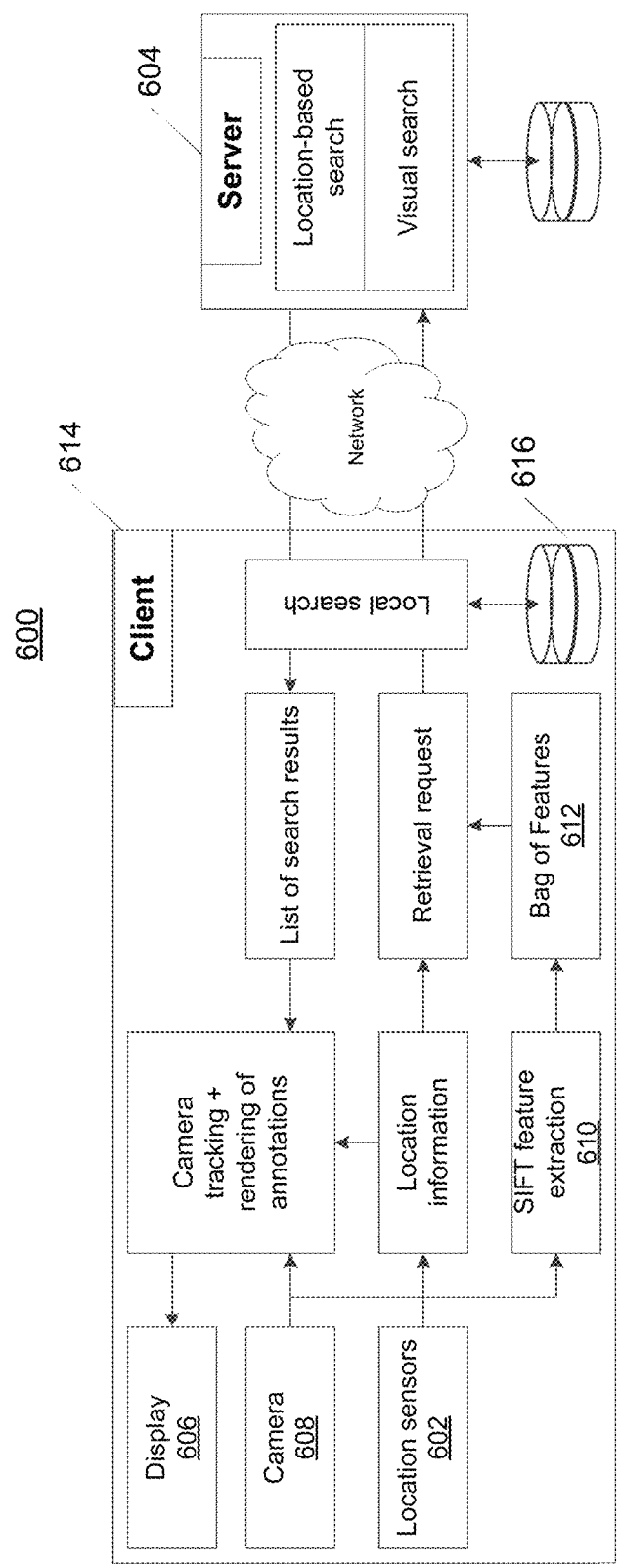
FIG. 6 is a block diagram illustrating an example AR system that may use location-based and visual search techniques.

FIG. 6 depicts an example AR system 600 that may use both location-based and visual search techniques. Location-based search may use input from sensors 602, such as GPS and wireless networks, to estimate a user's location. The location may be provided to a server 604, which may perform a search prior to presenting results to the user on the device's display 606. A visual search may be performed by extracting features, e.g., descriptors, from images that may be captured, for example, by a camera 608. This information may be sent as part of a request to the server 604. One example feature extraction algorithm is known as Scale Invariant Feature Transform (SIFT) 610, but other algorithms may be used. An image retrieval algorithm that may be used is known as "bag of features" 612. These features may be used to create a retrieval request that may be sent to the server 604 to obtain more relevant results. Other input methods, such as voice recognition, may be used to create a retrieval request.

The example AR system 600 may comprise a client 614 that may have capabilities to implement visual search and that may maintain a local database 616 to speed up computation and reduce network traffic. The local database 616 may be built up by collecting requests and corresponding results as they are sent to and received from the server 604. To maintain relevance of results and avoid providing stale results, the local database 616 may remove results after a period of time. The local database 616 may remove results using one or more location criteria, e.g., when the user changes location, some results may be removed from the cache because the results may be less likely to be needed again, or based on whether cached contents may still be viewable from the user's current location. For example, a content result may be removed from the cache based on a comparison of the user's current location to a location associated with the content result. As described herein, visual search may be implemented at the server, e.g., only at the server. In this case, local search may be omitted.

Figure 7:
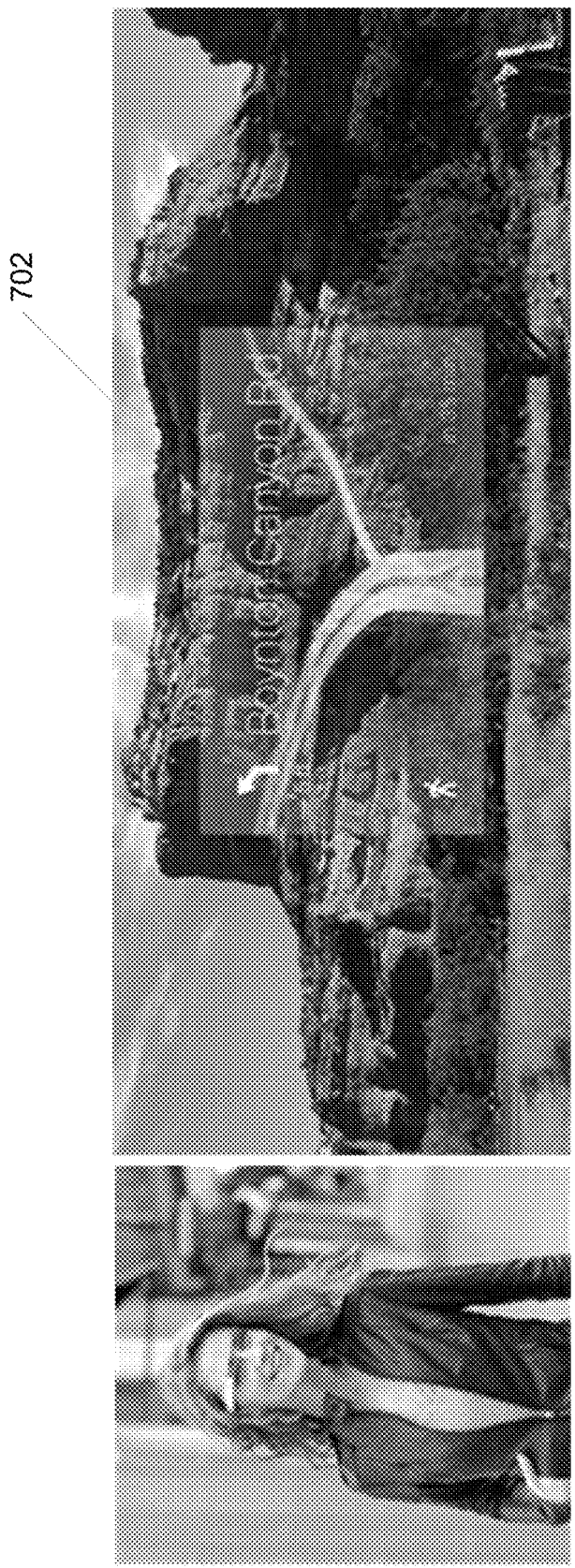
FIG. 7 is a diagram illustrating an example AR user interface.

FIG. 7 depicts an example AR user interface 702 that may be presented by an AR system, such as the GOOGLE GLASS® system. The AR user interface 702 may be used to allow users to perform functions that may be performed by smartphones. As shown in FIG. 7, a variety of information (e.g., icons, alerts, directional arrows, and/or other visual cues) may be displayed on the AR user interface 702, e.g., may be projected on the surface of a wearable electronic device. As AR becomes more closely integrated with wearable electronic devices, such as eyewear or contact lenses, visual search functionality will improve the functionality of such devices.

AR systems that have visual search functionality may enable retrieval of information about objects in the field of view of the camera. However, with some visual search techniques, at least some of the presented information may not be of interest to the user. Also, system and network resources may be used on searching results that the user is not interested in. Further, the user interface may be cumbersome to use.

According to the disclosed subject matter, the relevance of the information presented to the user of an AR system may be improved using a number of techniques individually or in combination. The gaze point of a user may be estimated, and information may be presented in the areas, (e.g., only in the areas) where the user is focusing his or her direction of view. The estimated gaze point of a user may be used to enable or facilitate modes of interactivity and/or user interfaces that may be controlled by the user's direction of view. Biometric techniques may be used to estimate the emotional state of a user to further refine the information that is presented to the user.

Figure 8:
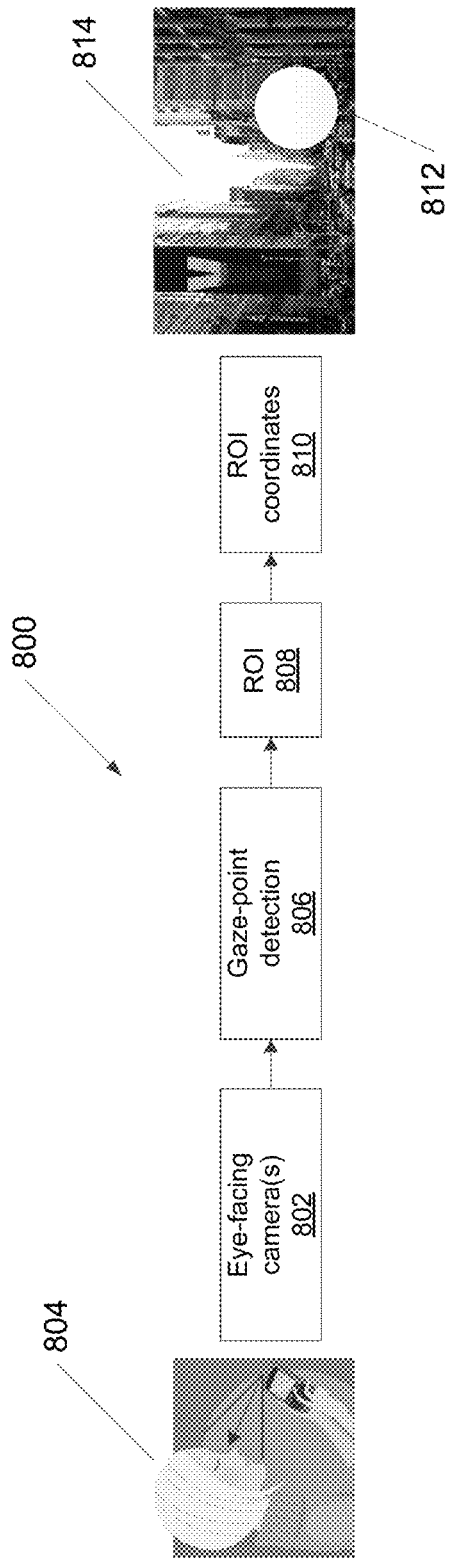
FIG. 8 is a block diagram illustrating an example gaze-point detection system.

A gaze-driven visual search engine may be used to improve the relevance and/or quality of search results in an AR system. FIG. 8 depicts an example gaze-point detection system 800. It will be appreciated that architectures other than the particular architecture shown in FIG. 8 may be implemented. A camera or cameras 802 facing a user 804 may capture one or more images, which may be used to determine the presence of human body features (e.g., face, nose, ears) to facilitate the identification of human eyes. If the camera or cameras 802 are located close to the face of the user, they may capture images of sufficient resolution to facilitate estimation of gaze point. For wearable devices, a camera may be placed on the device itself facing the user's eyes, enabling gaze-point detection.

A gaze-point detection subsystem 806 may use one or more eye gaze point direction estimation and/or detection techniques to estimate and/or detect a direction of view. A region of interest (ROI) subsystem 808 may determine coordinates 810 of a ROI 812 on an image 814 being captured by the camera. The size of the ROI and confidence level of accurate detection may be determined by the technique or techniques used for gaze-point detection. Either or both of these parameters may be used by the system 800 to determine the size of the ROI in which to perform a search.

Gaze-point detection may be based on any of a variety of technologies and may use devices mounted on the user's head or less intrusive systems (e.g., remote or non-head mounted systems). For example, a gaze-point detection system may analyze an image of the eye and may determine the gaze direction by computing the vector defined by the pupil center and a set of glints generated in the eye by an infrared illuminator. To increase the resolution of the vector, a camera with a narrow field of view may be used. Maintaining the eyes centered in the image, the camera may move to follow the eyes and compensate for the head movements.

Another example gaze-point detection system may allow combined tracking of the user's eye positions and the gaze direction in near real-time. Such a system may use two video cameras mounted on the left and right side of a display and may use facial feature detection to determine the position of the pupil in the eyes. A cornea-reflex method may be used to determine the gaze direction. For example, a low-power infrared-light emitting diode (LED) array may illuminate the eye and may generate a highlight on the cornea surface. An algorithm may identify and localize the center of both the pupil and the corneal surface reflection. The distance between the two centers and their orientation (e.g., gaze vector) may provide a measure of the gaze direction.

Figure 9:
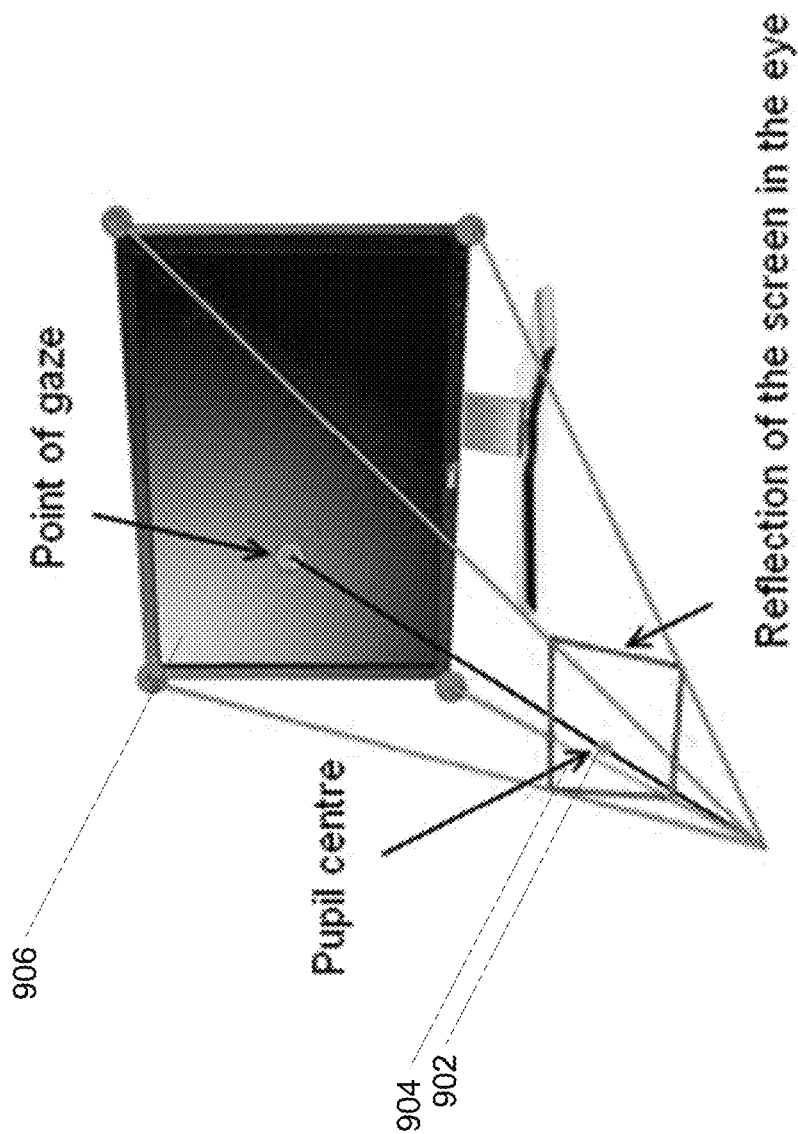
FIG. 9 illustrates an example eye tracking system.

FIG. 9 illustrates an example eye tracking system 900 that may use components, for example, including a webcam and infrared lighting. FIG. 9 illustrates how such a system may determine the direction of gaze, for example, based on a determined pupil center 902 and a reflection 904 of a screen 906 in the user's eye.

Figure 10:
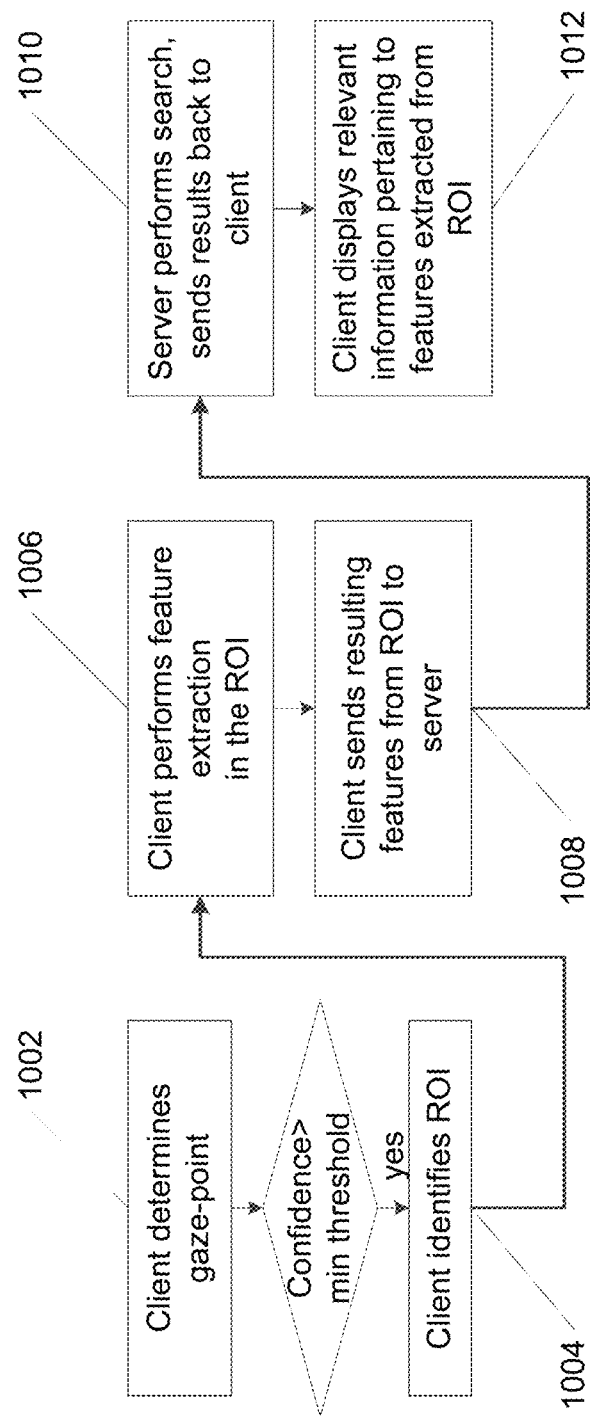
FIG. 10 illustrates an example of using gaze-point detection to limit a search over a region of interest (ROI).

FIG. 10 illustrates an example of using gaze-point detection to limit a search over a ROI. Features from the user's ROI may be sent to the server, where the search may take place. In a server-only approach, the server may perform feature extraction using the ROI information provided by the client. Communication with the server may be reduced by performing a local search first.

At 1002, a gaze-point may be determined. At 1004, the ROI may be identified, for example, by the client. After determining the user's ROI, the scope of the search may be further refined.

FIG. 11A illustrates that the same ROI may yield different results depending on the distance to the target. When the user is close to the target, only object A may be found in the search. If the user is far from the target, objects A-E may be found in the search. To address this situation, the size of the ROI may be adaptively adjusted when multiple objects of interest are found. This is illustrated in FIG. 11B, where the original ROI size is reduced in order to reduce the number of objects of interest. Adaptation of ROI size may be triggered by staring, by pushing a button, by voice command or automatically when the number of objects of interest is above a threshold.

Returning to FIG. 10, if the confidence of the determined gaze-point is greater than a minimum threshold, a ROI may be determined at 1004. The client may perform feature extraction in the ROI at 1006. The client may send the resulting features from the ROI to the server at 1008. The server may perform a search over the determined ROI and may return the results to the client at 1010. The client may display relevant information pertaining to features extracted from the ROI at 1012.

As a result of using gaze-point detection, a visual search may be focused in or around the ROI. Extracting relevant features from the ROI may reduce the processing requirements to conduct a search, reduce the amount of information that may be sent to the server, and/or improve the relevance of the results shown to the user.

A system may present results in the area where the user focuses his or her direction of view. A different use case may occur when the user is looking for particular objects and may not know where they are located. The user may provide input to the system (e.g., via voice command, keyboard or touch screen) to direct the search to the objects that the user is looking for. The input may be general (e.g., categories such as "museum" or "food") or specific (e.g., "Starbucks coffee"). The user may scan the field of view of the camera by directing his or her direction of view to different regions in the field of view of the camera. Results may be shown in the estimated ROI, allowing the user to determine whether the object is within the ROI. The user may temporarily disable the gaze-driven feature so that all results within the field of view of the camera are presented.

Gaze-point direction may be used to improve user interaction and/or facilitate or enable modes of interactivity in an AR system. For example, a user interface may be controlled by a user's direction of view. In this type of interface, a menu or set of choices may be shown on the display. The user may make choices using his or her eyes. This mode of interactivity may be more natural and may be faster than using hands, e.g., keyboard, mouse, and/or touch screen. For some systems, e.g., wearable systems, gaze-driven interactive processing may be a natural method for interaction, as peripherals that may be used for interaction, such as mouse and keyboard, may not be available.

Figure 12:
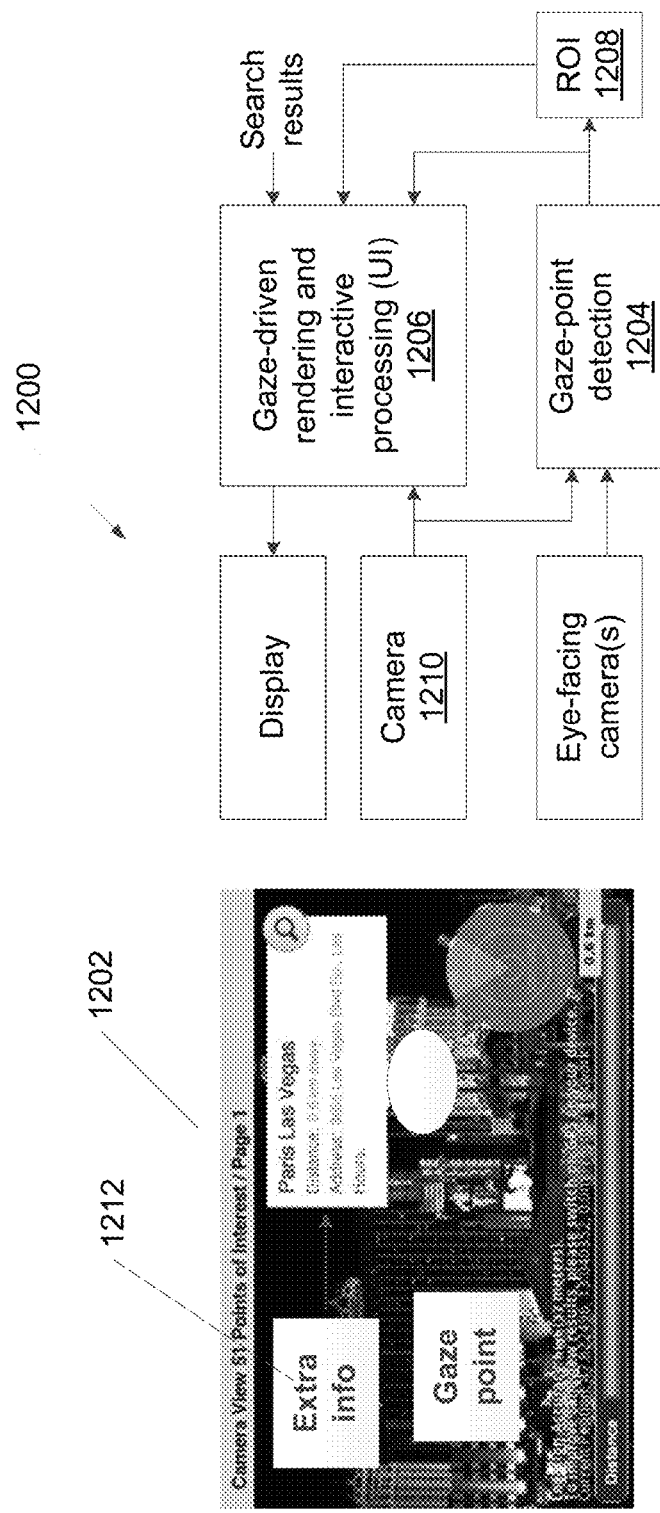
FIG. 12 depicts an example AR system comprising a gaze-driven user interface (UI).

FIG. 12 depicts an example AR system 1200 comprising a gaze-driven user interface (UI) 1202. Gaze-point detection may be determined by a gaze-point detection subsystem 1204. This information may be passed to an interactive processing (e.g., UI) engine 1206, where the gaze-point direction and ROI 1208 may be combined with input from a camera 1210 and/or results from location-based or visual search. Interactive processing may be achieved by determining if the user's gaze point corresponds to the location of an object of interest in the field of view of the camera. If so, the system may respond by taking an action that corresponds to the object of interest, for example, showing additional information 1212 on the object of interest, as shown in the user interface 1202.

Figure 13:
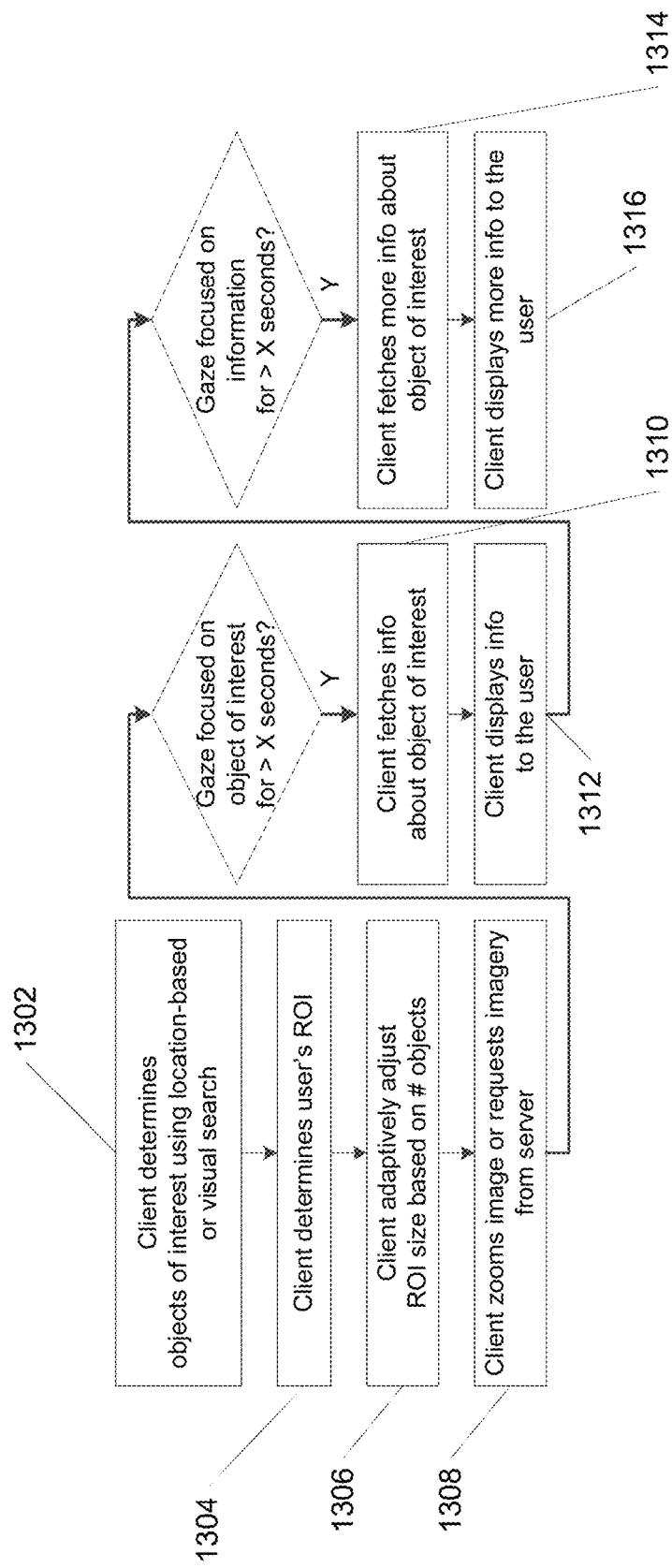
FIG. 13 illustrates an example of use of gaze-point detection on a gaze-driven user interface (UI).

FIG. 13 illustrates an example of use of gaze-point detection on a gaze-driven user interface. At 1302, the client may determine the objects of interest in the field of view of the camera. To improve system performance, a coarse visual search may be conducted first or location-based search may be used. At 1304, the user's ROI may be determined.

The user may be looking at a distant target that may have many objects of interest associated with it (e.g., a distant building with many small shops). In this case, the client may adaptively adjust the size of the ROI at 1306 to present only a subset of the objects of interest. In addition, at 1308, the objects may be arranged and/or the image may be zoomed such that the user is able to 'gaze trigger' the objects accurately. If the device is not be capable of zooming the image itself (e.g., the camera is not equipped with zoom or its capabilities are limited), additional imagery could be obtained from the server. The server may be able to provide a detailed picture that the device camera may not produce by camera zoom from the distance.

After the user's gaze has been focused on a ROI that contains an object of interest for a pre-determined number of seconds, the client may fetch information about the object either from the server or from a local database at 1310, and the information may be displayed to the user at 1312. To improve system performance, a limited amount of information may initially be fetched and shown to the user.

The user may obtain additional information about the object of interest by focusing on the information shown on the display. After the user's gaze has been focused on a ROI that contains the information for a pre-determined number of seconds, the client may fetch more information about the object at 1314 and display it to the user at 1316. The client may also call an external application (e.g., web browser or media player) instead of showing the additional information itself.

To increase the relevancy of search results in an AR system, the emotional state of the user may be inferred or estimated. Emotional state could include traditional emotional states, such as joy and anger, as well as physiological states (e.g., tiredness, alertness, and/or hunger) or psychological states (e.g., nervousness and/or anxiety) that may not traditionally be considered emotions. A variety of sensors, such as Galvanic Skin Response (GSR) and/or Electroencephalography (EEG), may be used to estimate the user's emotional state. Other methods (such as voice analysis, advanced computer vision techniques for recognizing emotion from facial expressions, biometrics and/or others) may also be used to perform this estimation, for example, as a point in a Valence/Arousal (V/A) chart.

Figure 14:
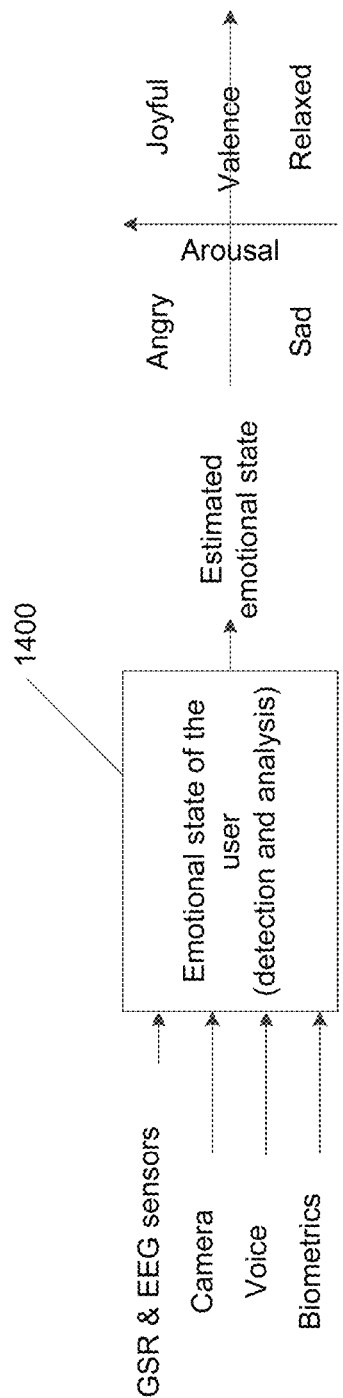
FIG. 14 is a block diagram illustrating an example module that may be used for estimating emotional state.

FIG. 14 illustrates an example module 1400 that may be used for estimating emotional state. The result may be used to filter and/or rank the search results that are presented to the user. For example, if the user is tired, choices related to food or beverages may rank higher than museums. As shown in FIG. 14, the module 1400 may receive as inputs data from GSR, EEG, and/or other sensors, camera data, voice data, and/or other biometric data. The module 1400 may output an estimated emotional state, which may have valence and arousal values and/or may map to descriptors such as angry, sad, joyful, and/or relaxed.

Estimating the emotional state of the user from various inputs may be done using one or more of the techniques described herein. Each of these techniques may yield a point in a V/A chart. Some or all of the inputs to the module may be available. The available points in the V/A chart may be combined to estimate the user's emotional state with some degree of confidence.

Galvanic skin response (GSR) may measure the electrical conductance of the skin. GSR may be highly sensitive to emotions (e.g., fear, anger, startle response) and sympathetic responses (e.g., aroused). GSR sensor data may be mapped to a user's emotional state. Electroencephalography (EEG) data may be used to detect user thoughts, feelings, and expressions and may have a high degree of temporal resolution.

Computer vision techniques may be used for recognizing emotion from the user's facial expressions and gestures. Age, gender, ethnicity, demographics, height, and weight may be estimated from camera input.

Speech analysis techniques (e.g., speech pattern recognition, machine learning, study of prosodic and acoustic features, vocal energy, speech rate, and pausing) may be used to estimate user's emotion.

Some smart headphones can measure biometric data such as heart rate, distance traveled, steps taken, respiration rate, speed, metabolic rate, energy expenditure, calories burned, recovery time, etc. Biometric data, such as respiration rate and heart rate, may be correlated to the emotional state of the user.

If multiple sensors are used in conjunction with one another, an emotional estimate may be computed using a mean operation to combine the output from the sensors. The mean operation may be performed in a weighted manner (for example, such that the output from sensors types that are more error prone may be weighted less than the output from sensors types that are more accurate). If a certain sensor does not produce an output, the weight for that output in a mean operation to determine an emotion estimate may be zero.

After obtaining an estimate of the user's emotional state, the result may be used to refine a retrieval request to the server or for local search, or to filter results that are presented to the user. For example, a user's emotional state may be used to restrict the search space by adding conditions in order to increase the relevance of the results. Points in the V/A chart may be mapped to categories of objects that may be used as qualifiers in the search terms. Therefore, search results may contain objects related to these search terms and may be more relevant to the user. For example, if the client estimates that the user is "Joyful", then terms such as "shopping" or "food" may be used. As another example, if the state is estimated to be "Relaxed", then terms such as "drink" or "art" may be used. Emotional state may also be used to filter and/or rank results to increase their relevance. For example, if the client estimates that the user is "Sad", then search results that are related to "health" or "music" may be ranked higher prior to presenting them to the user. As another example, if the state is estimated to be "Angry", then results related to "travel" or "nature" may be ranked higher.

Figure 15:
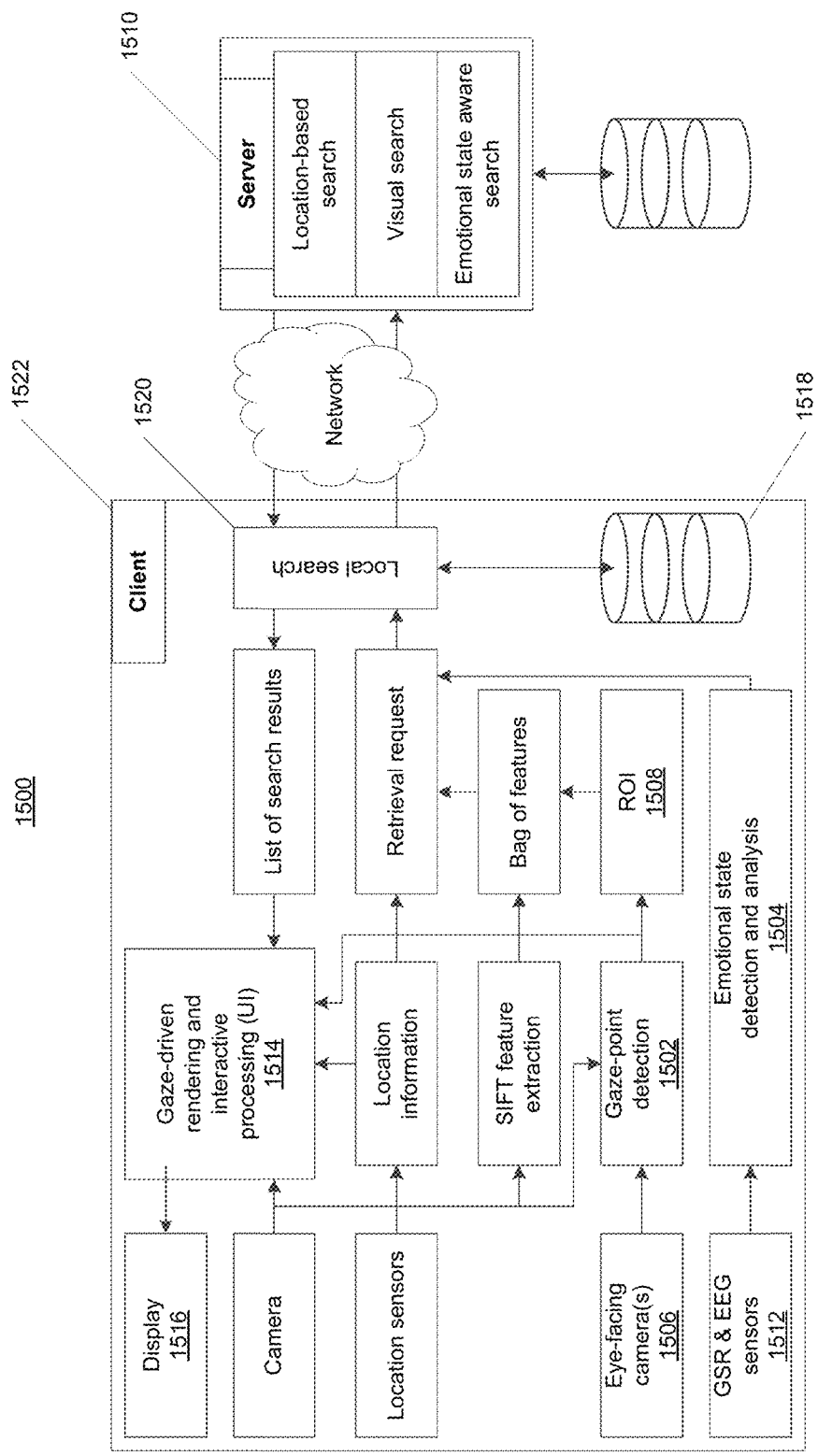
FIG. 15 is a block diagram illustrating an example gaze-driven AR system.

FIG. 15 illustrates an example gaze-driven AR system 1500. The gaze-driven AR system 1500 may comprise a gaze-point detection/estimation subsystem 1502 and/or an emotional state detection/estimation subsystem 1504. One or more eye-facing cameras 1506 may be used to enable gaze-point detection. This information may be used to determine a ROI 1508 on which search will be focused. Relevant features may be extracted from the ROI, (e.g., only from the ROI), potentially reducing the processing requirements to conduct a search and/or reducing the amount of information that may be sent to a server 1510.

A variety of sensors, such as Galvanic Skin Response (GSR) and Electroencephalography (EEG) sensors 1512, may be used to estimate the user's emotional state. Other methods, such as voice analysis or advanced image analysis techniques, may be used to perform this estimation. The results may be used to further narrow the search, potentially improving the quality of the results shown to the user.

A gaze-driven rendering and interactive processing module 1514 may enable users to interact with the results and options presented on a display 1516.

Gaze/visual search history may be stored and/or maintained in a local database 1518, e.g., as part of a local search module 1520. Keeping track of this history may reduce the burden on the network, as it may reduce traffic between clients and server. This may facilitate scaling the system to a large number of clients.

Search results may be improved by maintaining a profile of the user. The user may be able to configure search parameters, for example, by entering biometric or demographic information. Alternatively, with the user's permission, the system 1500 may infer this data by using sensors, cameras, and/or other methods. User profiles may be maintained locally at a client 1522 or at the server 1510.

Emotional responses may also be a useful guide in triggering visual search that is most relevant to the user. For example, if the system 1500 has detected on multiple occasions that a particular search result or a class of search results caused a reaction of disgust for the user, the search result or the class of search results may be lowered in priority in the future, or may be filtered out entirely. For example, the system 1500 may detect instances where the display of AR content for a particular sandwich shop ("Harry's sandwiches") causes a negative emotional response to the user, and as a result the system may give lower priority to the display of "Harry's Sandwich Shop" when it would appear in search results in the future. If the system 1500 were to subsequently detect a pattern where the display of AR content for multiple different sandwich shops caused a negative emotional response for the user, the system 1500 may give a lower priority to the display of sandwich shops generally, or may give a higher priority to the display of classes of restaurants other than sandwich shops. If the system 1500 has detected on multiple occasions that a particular search result or a class of search results caused a reaction of joy for the user (e.g. evoking a happy expression or a smile), then the search result or the class of search results may be given higher priority in the future. A history of emotional responses (e.g. multiple records comprising emotional response, date and/or time of the emotional response, and the AR content and/or real content which evoked the emotional response) may be kept locally or at the server 1510.

Gaze tracking may be used with wearable electronic devices, such as head-worn AR devices, e.g., the GOOGLE GLASS® system. Knowledge of user's gaze point may be used to localize search and improve relevance and effectiveness of annotations. Gaze point detection can also be used to facilitate or enable interactivity with AR applications. For example, by using gaze-driven visual search enhanced AR, search results may appear in the vicinity, e.g., only in the vicinity, of his/her gaze point. By focusing on a specific annotation, the user may invoke the expansion of the annotation into more detailed annotations with information about the object of interest.

Figure 16:
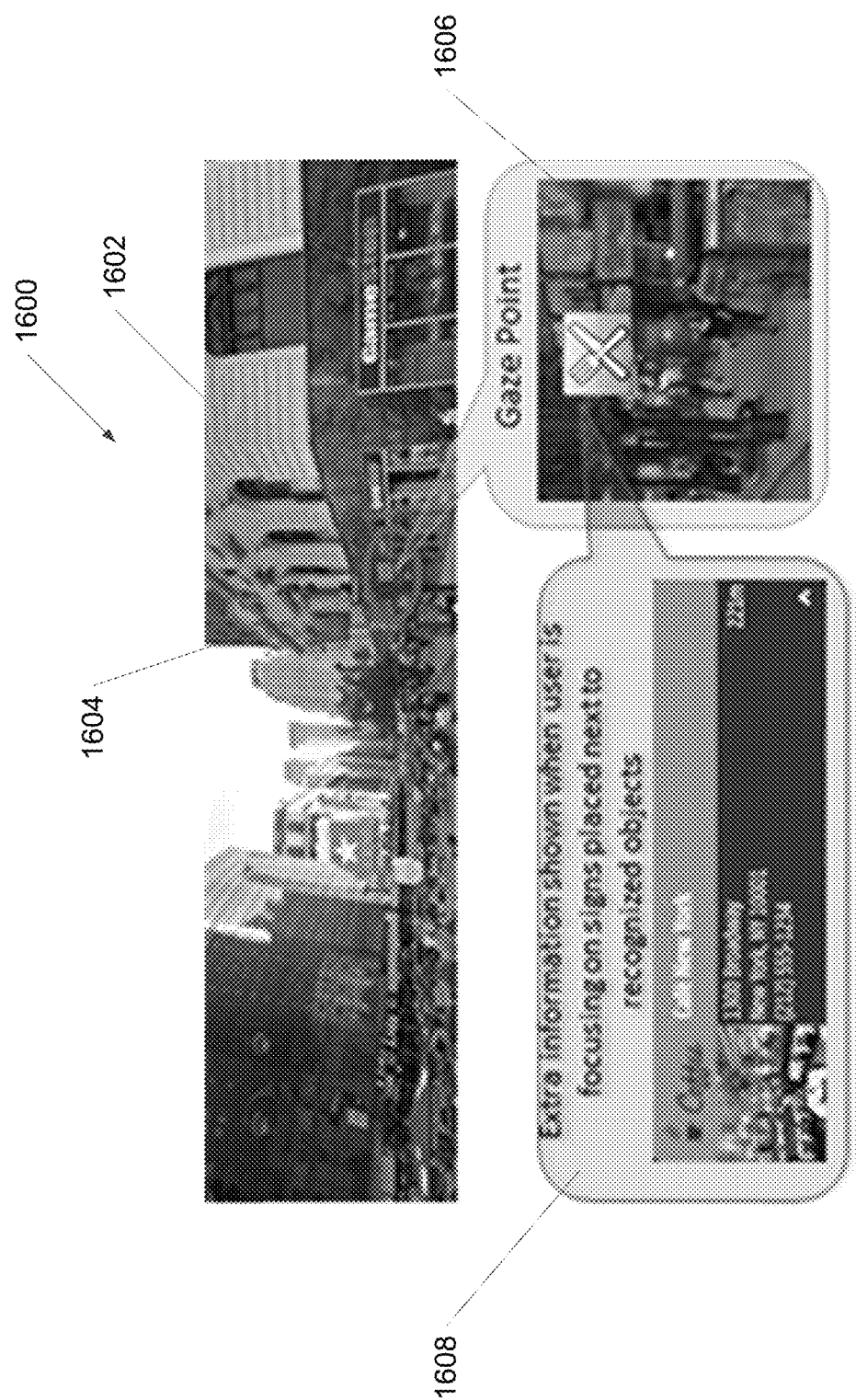
FIG. 16 is a diagram illustrating a gaze-driven AR user interface.

FIG. 16 illustrates a gaze-driven AR user interface 1600. In FIG. 16, an image 1602 represents the view seen by the user through the AR user interface. The user may focus his or her gaze, represented by a circle 1604, on signs placed next to recognized objects, e.g., a restaurant icon shown in a detailed image 1606. If the user focuses his or her view on a sign for a few seconds, extra information about the recognized object may be presented on the screen, shown in a detailed image 1608.

Figure 17:
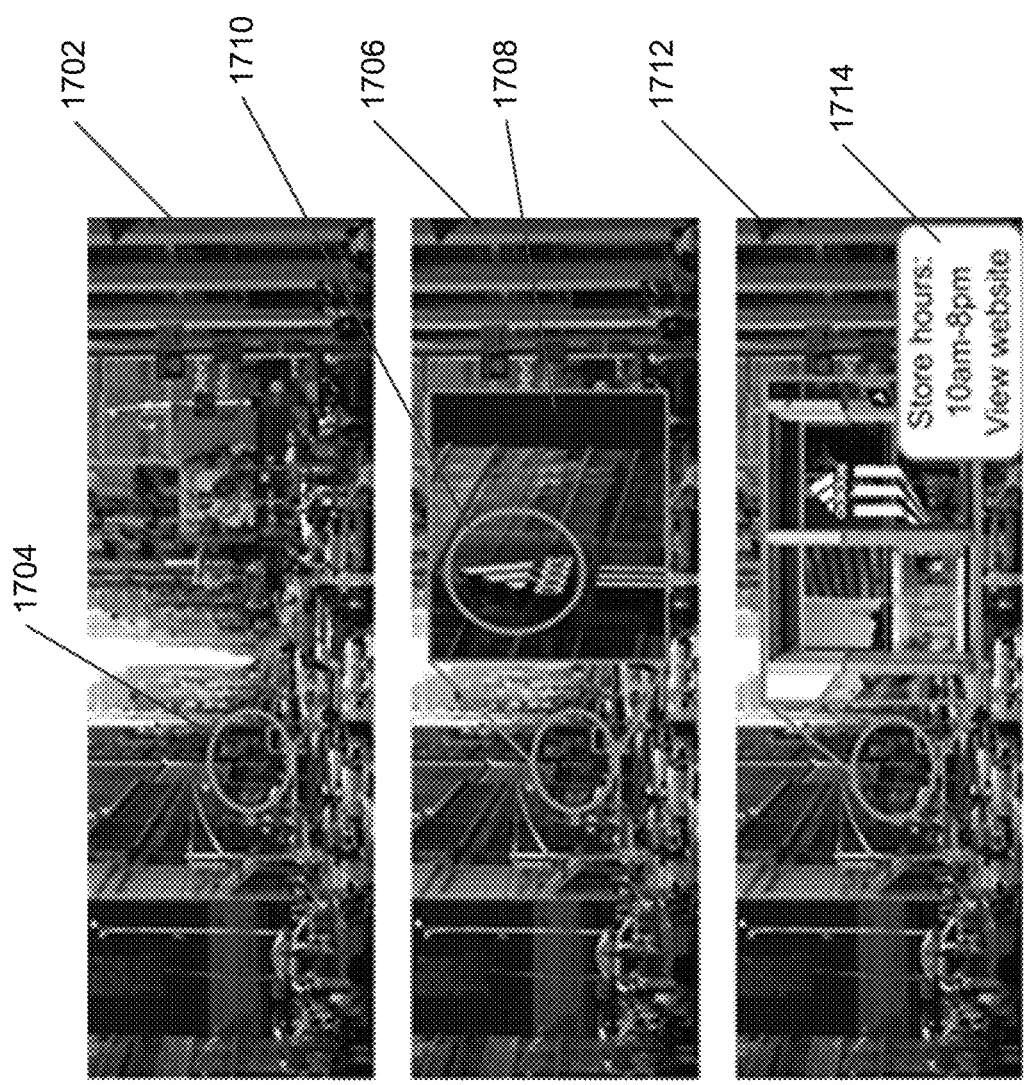
FIG. 17 depicts an example of adaptively adjusting a size of a ROI to reduce a number of objects of interest.

FIG. 17 depicts an example of adaptively adjusting a size of a ROI to reduce a number of objects of interest. An image 1702 represents the view seen by the user through an AR user interface. The user may focus his or her gaze on a ROI 1704. The client may determine an ROI. As shown in an image 1706, the ROI 1704 may contain a number of objects that may be of interest to the user. The client may adaptively adjust the ROI size to present a limited number of objects to the user in an overlapped window 1708. The user may focus his or her attention on an object within the new window 1708. The client may determine a new ROI 1710. As shown in an image 1712, the client may obtain additional imagery from server, as its zooming capabilities may be limited, and may present additional information to the user in a new window 1714 (e.g., "Store hours"). The user may focus his or her attention on the new window 1714, and the client may launch a new application (e.g., web browser).

The additional imagery from the server may include prerecorded images or video content. For example, the server may have a database of additional imagery previously recorded from locations of interest, from locations corresponding to businesses or landmarks, or from all locations visible from a street or from a set of streets. For example, the server may have a database of continuous street imagery indexed by geographical location, and such imagery may be used to display zoomed ROI images. For example, such imagery may be used to display more detailed images than those obtainable from a camera available on the user's device. The server may correlate and/or match the location of the user's gaze point in the physical world to the locations corresponding to the additional imagery, as indexed in the database, in order to identify suitable imagery to display for a given ROI.

The additional imagery from the server may include images or video content captured from a live camera. For example, the server may have access to one or more cameras which have views of locations of interest, of locations corresponding to businesses or landmarks, or of street views. Image and/or video content from a live camera may be available to the server via a fixed connection, or via a communication network. The server may correlate and/or match the location of the user's gaze point in the physical world to the locations of the available cameras, and in this way the server may locate a suitable camera and/or may determine whether a suitable camera is available. The server may communicate with a camera to obtain images and/or video content which correspond to a given ROI, and may transmit such images to the user device for display on the user device.

The additional imagery from the server displayed by the user device may be displayed together with information about objects of interest which are associated with the scope of the additional imagery. The user interface may allow the user to select objects of interest displayed in this way, or may allow the user to zoom further into the imagery using techniques disclosed herein.

The user interface may allow the user to pan within the additional imagery. For example, if the user device is a tablet computing device, the device may pan the imagery within the zoomed view shown in the image 1712 of FIG. 17 in response to the user moving the tablet computing device in a panning motion. As another example, if the user device is a wearable camera device with a head-mounted display, then the device may pan the imagery within the zoomed view shown in the image 1712 of FIG. 17 in response to panning head movements of the user. The user device may detect panning movements using orientation sensors on the user device, or may infer panning movements by detecting motion from a camera of the user device. The user device may send updated information to the server which describes the panning motion, the user device orientation, and/or the gaze point of the user. In response, the server may provide updated imagery that corresponds to the updated information, and the user device may display the updated imagery in order to pan within the additional imagery. In this way, the user may navigate within a magnified view of the physical world which may have more detail than could be captured using the camera available on the user's device.

Figure 18A:
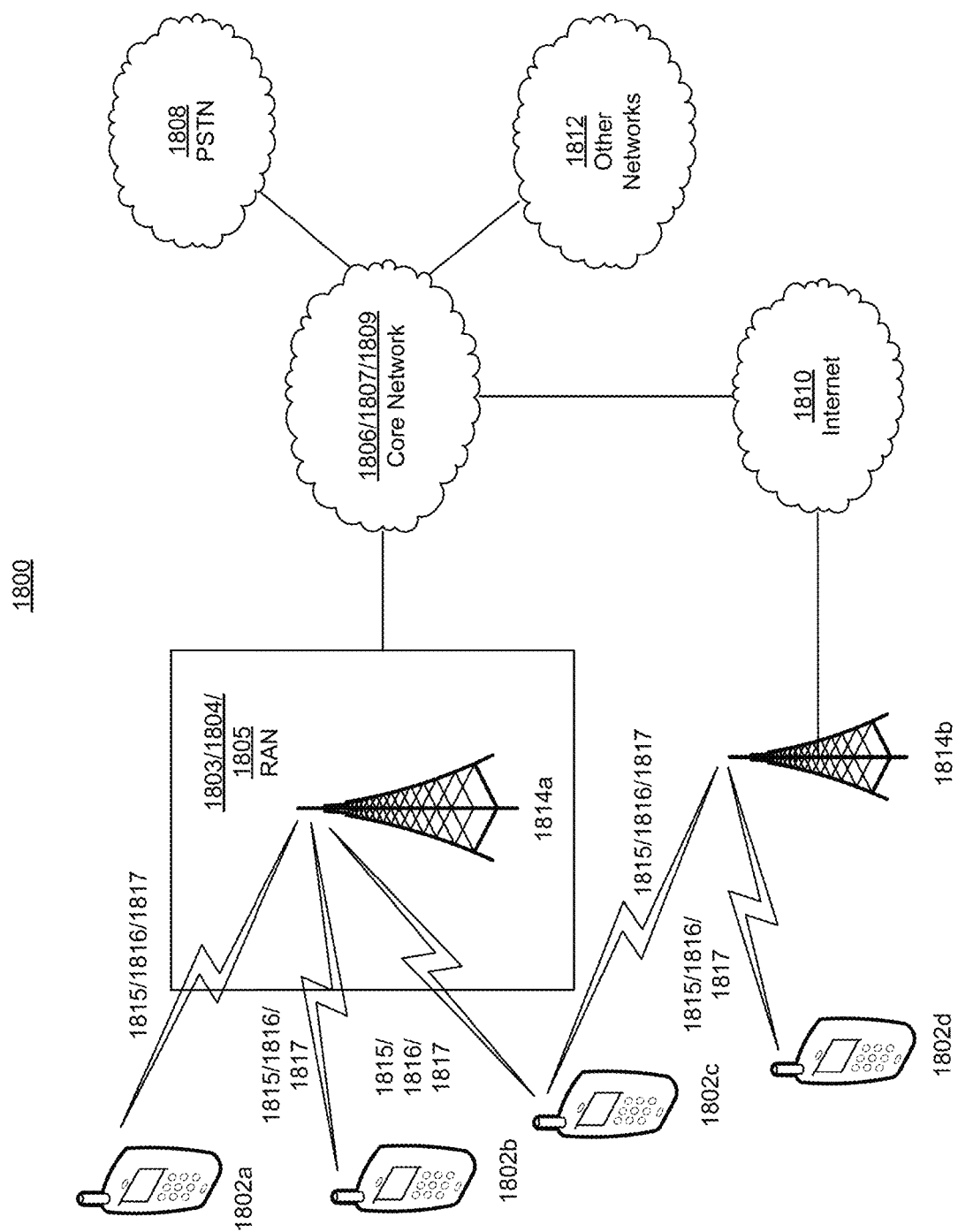
FIG. 18A is a system diagram of an example communications system in which one or more disclosed embodiments may be implemented.

FIG. 18A is a diagram of an example communications system 1800 in which one or more disclosed embodiments may be implemented. The communications system 1800 may be a multiple access system that provides content, such as voice, data, video, messaging, broadcast, etc., to multiple wireless users. The communications system 1800 may enable multiple wireless users to access such content through the sharing of system resources, including wireless bandwidth. For example, the communications systems 1800 may employ one or more channel access methods, such as code division multiple access (CDMA), time division multiple access (TDMA), frequency division multiple access (FDMA), orthogonal FDMA (OFDMA), single-carrier FDMA (SC-FDMA), and the like.

As shown in FIG. 18A, the communications system 1800 may include wireless transmit/receive units (WTRUs) 1802*a*, 1802*b*, 1802*c*, and/or 1802*d* (which generally or collectively may be referred to as WTRU 1802), a radio access network (RAN) 1803/1804/1805, a core network 1806/1807/1809, a public switched telephone network (PSTN) 1808, the Internet 1810, and other networks 1812, though it will be appreciated that the disclosed embodiments contemplate any number of WTRUs, base stations, networks, and/or network elements. Each of the WTRUs 1802*a*, 1802*b*, 1802*c*, 1802*d* may be any type of device configured to operate and/or communicate in a wireless environment. By way of example, the WTRUs 1802*a*, 1802*b*, 1802*c*, 1802*d* may be configured to transmit and/or receive wireless signals and may include user equipment (UE), a mobile station, a fixed or mobile subscriber unit, a pager, a cellular telephone, a personal digital assistant (PDA), a smartphone, a laptop, a netbook, a personal computer, a wireless sensor, consumer electronics, and the like.

The communications systems 1800 may also include a base station 1814*a* and a base station 1814*b*. Each of the base stations 1814*a*, 1814*b* may be any type of device configured to wirelessly interface with at least one of the WTRUs 1802*a*, 1802*b*, 1802*c*, 1802*d* to facilitate access to one or more communication networks, such as the core network 1806/1807/1809, the Internet 1810, and/or the networks 1812. By way of example, the base stations 1814*a*, 1814*b* may be a base transceiver station (BTS), a Node-B, an eNode B, a Home Node B, a Home eNode B, a site controller, an access point (AP), a wireless router, and the like. While the base stations 1814*a*, 1814*b* are each depicted as a single element, it will be appreciated that the base stations 1814*a*, 1814*b* may include any number of interconnected base stations and/or network elements.

The base station 1814*a* may be part of the RAN 1803/1804/1805, which may also include other base stations and/or network elements (not shown), such as a base station controller (BSC), a radio network controller (RNC), relay nodes, etc. The base station 1814*a* and/or the base station 1814*b* may be configured to transmit and/or receive wireless signals within a particular geographic region, which may be referred to as a cell (not shown). The cell may further be divided into cell sectors. For example, the cell associated with the base station 1814*a* may be divided into three sectors. Thus, in one embodiment, the base station 1814*a* may include three transceivers, e.g., one for each sector of the cell. In another embodiment, the base station 1814*a* may employ multiple-input multiple output (MIMO) technology and, therefore, may utilize multiple transceivers for each sector of the cell.

The base stations 1814*a*, 1814*b* may communicate with one or more of the WTRUs 1802*a*, 1802*b*, 1802*c*, 1802*d* over an air interface 1815/1816/1817, which may be any suitable wireless communication link (e.g., radio frequency (RF), microwave, infrared (IR), ultraviolet (UV), visible light, etc.). The air interface 1815/1816/1817 may be established using any suitable radio access technology (RAT).

More specifically, as noted above, the communications system 1800 may be a multiple access system and may employ one or more channel access schemes, such as CDMA, TDMA, FDMA, OFDMA, SC-FDMA, and the like. For example, the base station 1814*a* in the RAN 1803/1804/1805 and the WTRUs 1802*a*, 1802*b*, 1802*c* may implement a radio technology such as Universal Mobile Telecommunications System (UMTS) Terrestrial Radio Access (UTRA), which may establish the air interface 1815/1816/1817 using wideband CDMA (WCDMA). WCDMA may include communication protocols such as High-Speed Packet Access (HSPA) and/or Evolved HSPA (HSPA+). HSPA may include High-Speed Downlink Packet Access (HSDPA) and/or High-Speed Uplink Packet Access (HSUPA).

In another embodiment, the base station 1814*a* and the WTRUs 1802*a*, 1802*b*, 1802*c* may implement a radio technology such as Evolved UMTS Terrestrial Radio Access (E-UTRA), which may establish the air interface 1815/1816/1817 using Long Term Evolution (LTE) and/or LTE-Advanced (LTE-A).

In other embodiments, the base station 1814*a* and the WTRUs 1802*a*, 1802*b*, 1802*c* may implement radio technologies such as IEEE 802.16 (e.g., Worldwide Interoperability for Microwave Access (WiMAX)), CDMA2000, CDMA2000 1x, CDMA2000 EV-DO, Interim Standard 2000 (IS-2000), Interim Standard 95 (IS-95), Interim Standard 856 (IS-856), Global System for Mobile communications (GSM), Enhanced Data rates for GSM Evolution (EDGE), GSM EDGE (GERAN), and the like.

The base station 1814b in FIG. 18A may be a wireless router, Home Node B, Home eNode B, or access point, for example, and may utilize any suitable RAT for facilitating wireless connectivity in a localized area, such as a place of business, a home, a vehicle, a campus, and the like. In one embodiment, the base station 1814b and the WTRUs 1802c, 1802d may implement a radio technology such as IEEE 802.11 to establish a wireless local area network (WLAN). In another embodiment, the base station 1814b and the WTRUs 1802c, 1802d may implement a radio technology such as IEEE 802.15 to establish a wireless personal area network (WPAN). In yet another embodiment, the base station 1814b and the WTRUs 1802c, 1802d may utilize a cellular-based RAT (e.g., WCDMA, CDMA2000, GSM, LTE, LTE-A, etc.) to establish a picocell or femtocell. As shown in FIG. 18A, the base station 1814b may have a direct connection to the Internet 1810. Thus, the base station 1814b may not be required to access the Internet 1810 via the core network 1806/1807/1809.

The RAN 1803/1804/1805 may be in communication with the core network 1806/1807/1809, which may be any type of network configured to provide voice, data, applications, and/or voice over internet protocol (VoIP) services to one or more of the WTRUs 1802a, 1802b, 1802c, 1802d. For example, the core network 1806/1807/1809 may provide call control, billing services, mobile location-based services, pre-paid calling, Internet connectivity, video distribution, etc., and/or perform high-level security functions, such as user authentication. Although not shown in FIG. 18A, it will be appreciated that the RAN 1803/1804/1805 and/or the core network 1806/1807/1809 may be in direct or indirect communication with other RANs that employ the same RAT as the RAN 1803/1804/1805 or a different RAT. For example, in addition to being connected to the RAN 1803/1804/1805, which may be utilizing an E-UTRA radio technology, the core network 1806/1807/1809 may also be in communication with another RAN (not shown) employing a GSM radio technology.

The core network 1806/1807/1809 may also serve as a gateway for the WTRUs 1802a, 1802b, 1802c, 1802d to access the PSTN 1808, the Internet 1810, and/or other networks 1812. The PSTN 1808 may include circuit-switched telephone networks that provide plain old telephone service (POTS). The Internet 1810 may include a global system of interconnected computer networks and devices that use common communication protocols, such as the transmission control protocol (TCP), user datagram protocol (UDP) and the internet protocol (IP) in the TCP/IP internet protocol suite. The networks 1812 may include wired or wireless communications networks owned and/or operated by other service providers. For example, the networks 1812 may include another core network connected to one or more RANs, which may employ the same RAT as the RAN 1803/1804/1805 or a different RAT.

Some or all of the WTRUs 1802a, 1802b, 1802c, 1802d in the communications system 1800 may include multi-mode capabilities, e.g., the WTRUs 1802a, 1802b, 1802c, 1802d may include multiple transceivers for communicating with different wireless networks over different wireless links. For example, the WTRU 1802c shown in FIG. 18A may be configured to communicate with the base station 1814a, which may employ a cellular-based radio technology, and with the base station 1814b, which may employ an IEEE 802 radio technology.

Figure 18B:
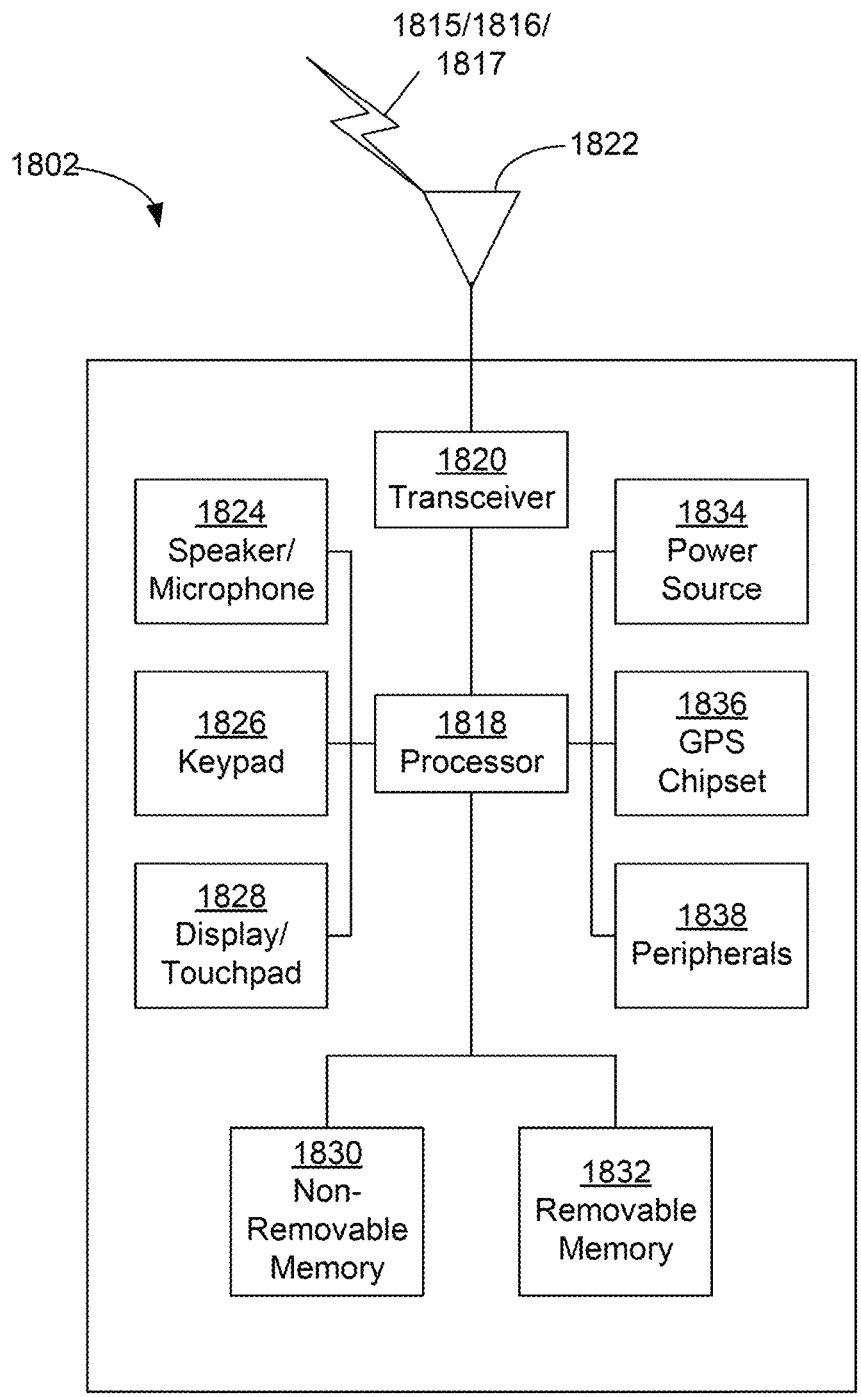
FIG. 18B is a system diagram of an example wireless transmit/receive unit (WTRU) that may be used within the communications system illustrated in FIG. 18A.

FIG. 18B is a system diagram of an example WTRU 1802. As shown in FIG. 18B, the WTRU 1802 may include a processor 1818, a transceiver 1820, a transmit/receive element 1822, a speaker/microphone 1824, a keypad 1826, a display/touchpad 1828, non-removable memory 1830, removable memory 1832, a power source 1834, a global positioning system (GPS) chipset 1836, and other peripherals 1838. It will be appreciated that the WTRU 1802 may include any sub-combination of the foregoing elements while remaining consistent with an embodiment. Also, embodiments contemplate that the base stations 1814a and 1814b, and/or the nodes that base stations 1814a and 1814b may represent, such as but not limited to transceiver station (BTS), a Node-B, a site controller, an access point (AP), a home node-B, an evolved home node-B (eNodeB), a home evolved node-B (HeNB or HeNodeB), a home evolved node-B gateway, and proxy nodes, among others, may include some or all of the elements depicted in FIG. 18B and described herein.

The processor 1818 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGAs) circuits, any other type of integrated circuit (IC), a state machine, and the like. The processor 1818 may perform signal coding, data processing, power control, input/output processing, and/or any other functionality that enables the WTRU 1802 to operate in a wireless environment. The processor 1818 may be coupled to the transceiver 1820, which may be coupled to the transmit/receive element 1822. While FIG. 18B depicts the processor 1818 and the transceiver 1820 as separate components, it will be appreciated that the processor 1818 and the transceiver 1820 may be integrated together in an electronic package or chip.

The transmit/receive element 1822 may be configured to transmit signals to, or receive signals from, a base station (e.g., the base station 1814a) over the air interface 1815/1816/1817. For example, in one embodiment, the transmit/receive element 1822 may be an antenna configured to transmit and/or receive RF signals. In another embodiment, the transmit/receive element 1822 may be an emitter/detector configured to transmit and/or receive IR, UV, or visible light signals, for example. In yet another embodiment, the transmit/receive element 1822 may be configured to transmit and receive both RF and light signals. It will be appreciated that the transmit/receive element 1822 may be configured to transmit and/or receive any combination of wireless signals.

In addition, although the transmit/receive element 1822 is depicted in FIG. 18B as a single element, the WTRU 1802 may include any number of transmit/receive elements 1822. More specifically, the WTRU 1802 may employ MIMO technology. Thus, in one embodiment, the WTRU 1802 may include two or more transmit/receive elements 1822 (e.g., multiple antennas) for transmitting and receiving wireless signals over the air interface 1815/1816/1817.

The transceiver 1820 may be configured to modulate the signals that are to be transmitted by the transmit/receive element 1822 and to demodulate the signals that are received by the transmit/receive element 1822. As noted above, the WTRU 1802 may have multi-mode capabilities. Thus, the transceiver 1820 may include multiple transceivers for enabling the WTRU 1802 to communicate via multiple RATs, such as UTRA and IEEE 802.11, for example.

The processor 1818 of the WTRU 1802 may be coupled to, and may receive user input data from, the speaker/microphone 1824, the keypad 1826, and/or the display/touchpad 1828 (e.g., a liquid crystal display (LCD) display unit or organic light-emitting diode (OLED) display unit). The processor 1818 may also output user data to the speaker/microphone 1824, the keypad 1826, and/or the display/touchpad 1828. In addition, the processor 1818 may access information from, and store data in, any type of suitable memory, such as the non-removable memory 1830 and/or the removable memory 1832. The non-removable memory 1830 may include random-access memory (RAM), read-only memory (ROM), a hard disk, or any other type of memory storage device. The removable memory 1832 may include a subscriber identity module (SIM) card, a memory stick, a secure digital (SD) memory card, and the like. In other embodiments, the processor 1818 may access information from, and store data in, memory that is not physically located on the WTRU 1802, such as on a server or a home computer (not shown).

The processor 1818 may receive power from the power source 1834, and may be configured to distribute and/or control the power to the other components in the WTRU 1802. The power source 1834 may be any suitable device for powering the WTRU 1802. For example, the power source 1834 may include one or more dry cell batteries (e.g., nickel-cadmium (NiCd), nickel-zinc (NiZn), nickel metal hydride (NiMH), lithium-ion (Li-ion), etc.), solar cells, fuel cells, and the like.

The processor 1818 may also be coupled to the GPS chipset 1836, which may be configured to provide location information (e.g., longitude and latitude) regarding the current location of the WTRU 1802. In addition to, or in lieu of, the information from the GPS chipset 1836, the WTRU 1802 may receive location information over the air interface 1815/1816/1817 from a base station (e.g., base stations 1814a, 1814b) and/or determine its location based on the timing of the signals being received from two or more nearby base stations. It will be appreciated that the WTRU 1802 may acquire location information by way of any suitable location-determination implementation while remaining consistent with an embodiment.

The processor 1818 may further be coupled to other peripherals 1838, which may include one or more software and/or hardware modules that provide additional features, functionality and/or wired or wireless connectivity. For example, the peripherals 1838 may include an accelerometer, an e-compass, a satellite transceiver, a digital camera (for photographs or video), a universal serial bus (USB) port, a vibration device, a television transceiver, a hands free headset, a Bluetooth® module, a frequency modulated (FM) radio unit, a digital music player, a media player, a video game player module, an Internet browser, and the like.

Figure 18C:
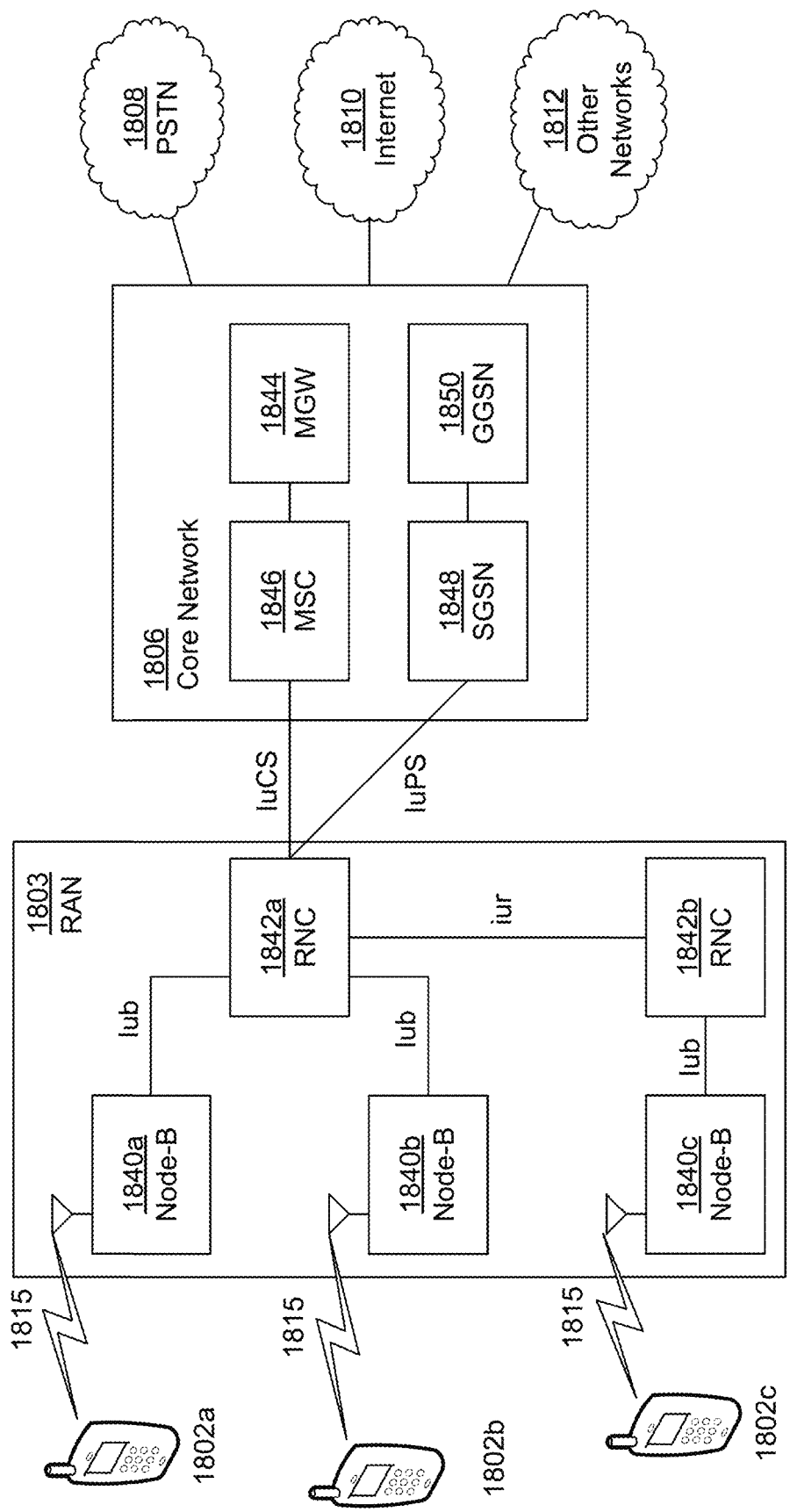
FIG. 18C is a system diagram of an example radio access network and an example core network that may be used within the communications system illustrated in FIG. 18A.

FIG. 18C is a system diagram of the RAN 1803 and the core network 1806 according to an embodiment. As noted above, the RAN 1803 may employ a UTRA radio technology to communicate with the WTRUs 1802a, 1802b, 1802c over the air interface 1815. The RAN 1803 may also be in communication with the core network 1806. As shown in FIG. 18C, the RAN 1803 may include Node-Bs 1840a, 1840b, 1840c, which may each include one or more transceivers for communicating with the WTRUs 1802a, 1802b, 1802c over the air interface 1815. The Node-Bs 1840a, 1840b, 1840c may each be associated with a particular cell (not shown) within the RAN 1803. The RAN 1803 may also include RNCs 1842a, 1842b. It will be appreciated that the RAN 1803 may include any number of Node-Bs and RNCs while remaining consistent with an embodiment.

As shown in FIG. 18C, the Node-Bs 1840a, 1840b may be in communication with the RNC 1842a. Additionally, the Node-B 1840c may be in communication with the RNC 1842b. The Node-Bs 1840a, 1840b, 1840c may communicate with the respective RNCs 1842a, 1842b via an Iub interface. The RNCs 1842a, 1842b may be in communication with one another via an Iur interface. Each of the RNCs 1842a, 1842b may be configured to control the respective Node-Bs 1840a, 1840b, 1840c to which it is connected. In addition, each of the RNCs 1842a, 1842b may be configured to carry out or support other functionality, such as outer loop power control, load control, admission control, packet scheduling, handover control, macrodiversity, security functions, data encryption, and the like.

The core network 1806 shown in FIG. 18C may include a media gateway (MGW) 1844, a mobile switching center (MSC) 1846, a serving GPRS support node (SGSN) 1848, and/or a gateway GPRS support node (GGSN) 1850. While each of the foregoing elements are depicted as part of the core network 1806, it will be appreciated that any one of these elements may be owned and/or operated by an entity other than the core network operator.

The RNC 1842a in the RAN 1803 may be connected to the MSC 1846 in the core network 1806 via an IuCS interface. The MSC 1846 may be connected to the MGW 1844. The MSC 1846 and the MGW 1844 may provide the WTRUs 1802a, 1802b, 1802c with access to circuit-switched networks, such as the PSTN 1808, to facilitate communications between the WTRUs 1802a, 1802b, 1802c and traditional land-line communications devices.

The RNC 1842a in the RAN 1803 may also be connected to the SGSN 1848 in the core network 1806 via an IuPS interface. The SGSN 1848 may be connected to the GGSN 1850. The SGSN 1848 and the GGSN 1850 may provide the WTRUs 1802a, 1802b, 1802c with access to packet-switched networks, such as the Internet 1810, to facilitate communications between and the WTRUs 1802a, 1802b, 1802c and IP-enabled devices.

As noted above, the core network 1806 may also be connected to the networks 1812, which may include other wired or wireless networks that are owned and/or operated by other service providers.

Figure 18D:
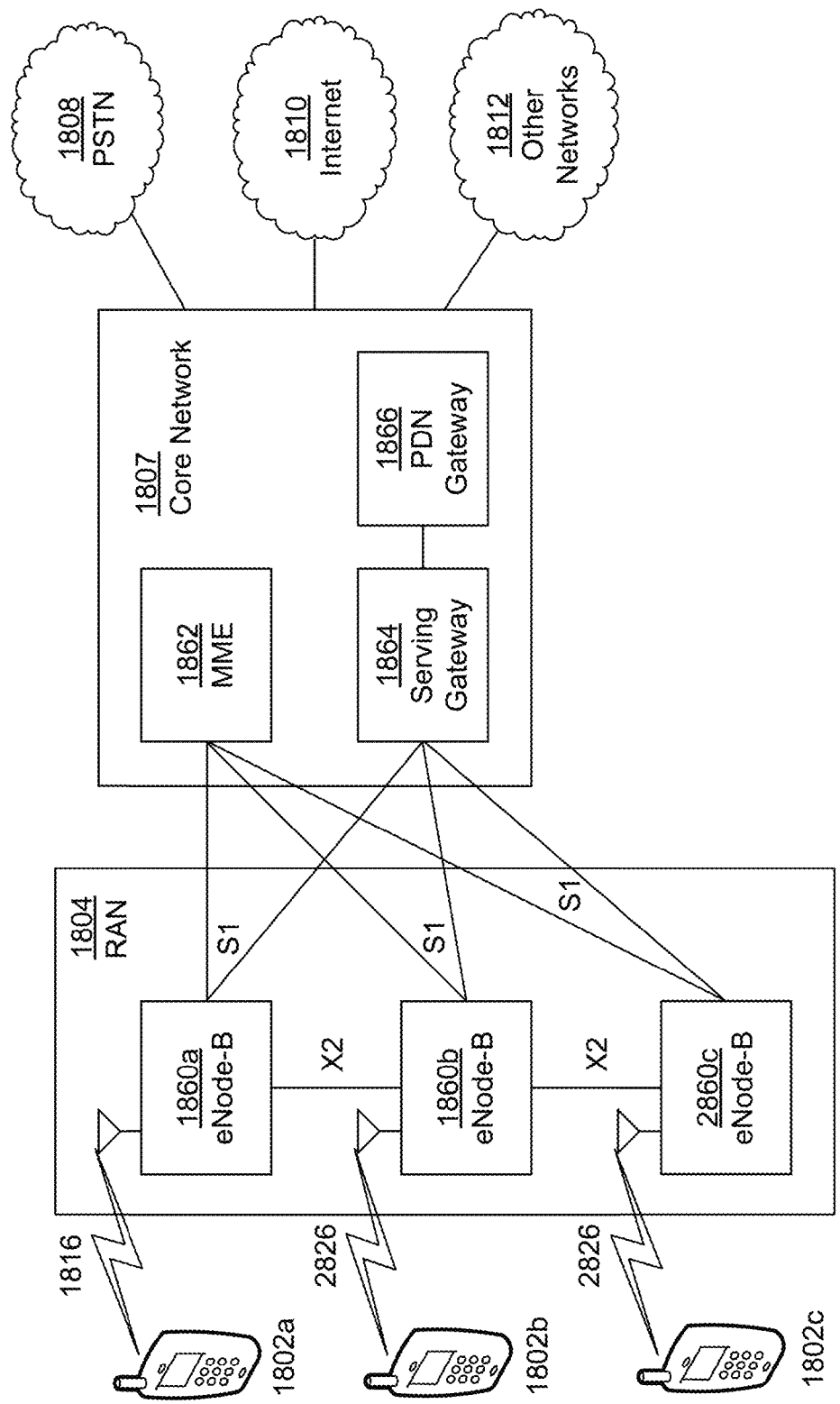
FIG. 18D is a system diagram of another example radio access network and another example core network that may be used within the communications system illustrated in FIG. 18A.

FIG. 18D is a system diagram of the RAN 1804 and the core network 1807 according to an embodiment. As noted above, the RAN 1804 may employ an E-UTRA radio technology to communicate with the WTRUs 1802a, 1802b, 1802c over the air interface 1816. The RAN 1804 may also be in communication with the core network 1807.

The RAN 1804 may include eNode-Bs 1860a, 1860b, 1860c, though it will be appreciated that the RAN 1804 may include any number of eNode-Bs while remaining consistent with an embodiment. The eNode-Bs 1860a, 1860b, 1860c may each include one or more transceivers for communicating with the WTRUs 1802a, 1802b, 1802c over the air interface 1816. In one embodiment, the eNode-Bs 1860a, 1860b, 1860c may implement MIMO technology. Thus, the eNode-B 1860a, for example, may use multiple antennas to transmit wireless signals to, and receive wireless signals from, the WTRU 1802a.

Each of the eNode-Bs 1860a, 1860b, 1860c may be associated with a particular cell (not shown) and may be configured to handle radio resource management decisions, handover decisions, scheduling of users in the uplink and/or downlink, and the like. As shown in FIG. 18D, the eNode-Bs 1860a, 1860b, 1860c may communicate with one another over an X2 interface.

The core network 1807 shown in FIG. 18D may include a mobility management gateway (MME) 1862, a serving gateway 1864, and a packet data network (PDN) gateway 1866. While each of the foregoing elements are depicted as part of the core network 1807, it will be appreciated that any one of these elements may be owned and/or operated by an entity other than the core network operator.

The MME 1862 may be connected to each of the eNode-Bs 1860a, 1860b, 1860c in the RAN 1804 via an S1 interface and may serve as a control node. For example, the MME 1862 may be responsible for authenticating users of the WTRUs 1802a, 1802b, 1802c, bearer activation/deactivation, selecting a particular serving gateway during an initial attach of the WTRUs 1802a, 1802b, 1802c, and the like. The MME 1862 may also provide a control plane function for switching between the RAN 1804 and other RANs (not shown) that employ other radio technologies, such as GSM or WCDMA.

The serving gateway 1864 may be connected to each of the eNode-Bs 1860a, 1860b, 1860c in the RAN 1804 via the S1 interface. The serving gateway 1864 may generally route and forward user data packets to/from the WTRUs 1802a, 1802b, 1802c. The serving gateway 1864 may also perform other functions, such as anchoring user planes during inter-eNode B handovers, triggering paging when downlink data is available for the WTRUs 1802a, 1802b, 1802c, managing and storing contexts of the WTRUs 1802a, 1802b, 1802c, and the like.

The serving gateway 1864 may also be connected to the PDN gateway 1866, which may provide the WTRUs 1802a, 1802b, 1802c with access to packet-switched networks, such as the Internet 1810, to facilitate communications between the WTRUs 1802a, 1802b, 1802c and IP-enabled devices.

The core network 1807 may facilitate communications with other networks. For example, the core network 1807 may provide the WTRUs 1802a, 1802b, 1802c with access to circuit-switched networks, such as the PSTN 1808, to facilitate communications between the WTRUs 1802a, 1802b, 1802c and traditional land-line communications devices. For example, the core network 1807 may include, or may communicate with, an IP gateway (e.g., an IP multimedia subsystem (IMS) server) that serves as an interface between the core network 1807 and the PSTN 1808. In addition, the core network 1807 may provide the WTRUs 1802a, 1802b, 1802c with access to the networks 1812, which may include other wired or wireless networks that are owned and/or operated by other service providers.

Figure 18E:
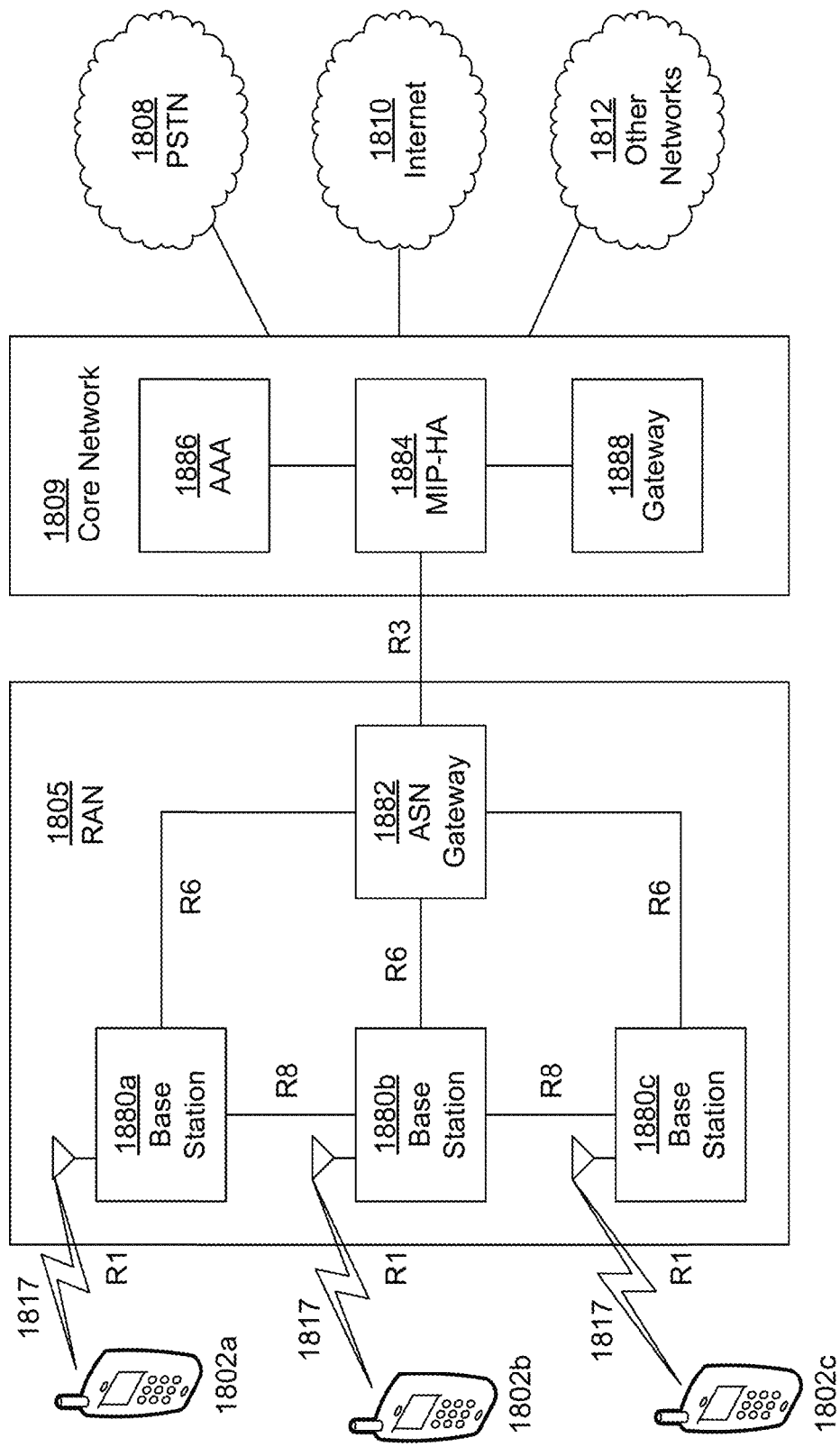
FIG. 18E is a system diagram of another example radio access network and another example core network that may be used within the communications system illustrated in FIG. 18A.

FIG. 18E is a system diagram of the RAN 1805 and the core network 1809 according to an embodiment. The RAN 1805 may be an access service network (ASN) that employs IEEE 802.16 radio technology to communicate with the WTRUs 1802a, 1802b, 1802c over the air interface 1817. As will be further discussed below, the communication links between the different functional entities of the WTRUs 1802a, 1802b, 1802c, the RAN 1805, and the core network 1809 may be defined as reference points.

As shown in FIG. 18E, the RAN 1805 may include base stations 1880a, 1880b, 1880c, and an ASN gateway 1882, though it will be appreciated that the RAN 1805 may include any number of base stations and ASN gateways while remaining consistent with an embodiment. The base stations 1880a, 1880b, 1880c may each be associated with a particular cell (not shown) in the RAN 1805 and may each include one or more transceivers for communicating with the WTRUs 1802a, 1802b, 1802c over the air interface 1817. In one embodiment, the base stations 1880a, 1880b, 1880c may implement MIMO technology. Thus, the base station 1880a, for example, may use multiple antennas to transmit wireless signals to, and receive wireless signals from, the WTRU 1802a. The base stations 1880a, 1880b, 1880c may also provide mobility management functions, such as handoff triggering, tunnel establishment, radio resource management, traffic classification, quality of service (QoS) policy enforcement, and the like. The ASN gateway 1882 may serve as a traffic aggregation point and may be responsible for paging, caching of subscriber profiles, routing to the core network 1809, and the like.

The air interface 1817 between the WTRUs 1802a, 1802b, 1802c and the RAN 1805 may be defined as an R1 reference point that implements the IEEE 802.16 specification. In addition, each of the WTRUs 1802a, 1802b, 1802c may establish a logical interface (not shown) with the core network 1809. The logical interface between the WTRUs 1802a, 1802b, 1802c and the core network 1809 may be defined as an R2 reference point, which may be used for authentication, authorization, IP host configuration management, and/or mobility management.

The communication link between each of the base stations 1880a, 1880b, 1880c may be defined as an R8 reference point that includes protocols for facilitating WTRU handovers and the transfer of data between base stations. The communication link between the base stations 1880a, 1880b, 1880c and the ASN gateway 1882 may be defined as an R6 reference point. The R6 reference point may include protocols for facilitating mobility management based on mobility events associated with each of the WTRUs 1802a, 1802b, 1802c.

As shown in FIG. 18E, the RAN 1805 may be connected to the core network 1809. The communication link between the RAN 1805 and the core network 1809 may defined as an R3 reference point that includes protocols for facilitating data transfer and mobility management capabilities, for example. The core network 1809 may include a mobile IP home agent (MIP-HA) 1884, an authentication, authorization, accounting (AAA) server 1886, and a gateway 1888. While each of the foregoing elements are depicted as part of the core network 1809, it will be appreciated that any one of these elements may be owned and/or operated by an entity other than the core network operator.

The MIP-HA may be responsible for IP address management, and may enable the WTRUs 1802a, 1802b, 1802c to roam between different ASNs and/or different core networks. The MIP-HA 1884 may provide the WTRUs 1802a, 1802b, 1802c with access to packet-switched networks, such as the Internet 1810, to facilitate communications between the WTRUs 1802a, 1802b, 1802c and IP-enabled devices. The AAA server 1886 may be responsible for user authentication and for supporting user services. The gateway 1888 may facilitate interworking with other networks. For example, the gateway 1888 may provide the WTRUs 1802a, 1802b, 1802c with access to circuit-switched networks, such as the PSTN 1808, to facilitate communications between the WTRUs 1802a, 1802b, 1802c and traditional land-line communications devices. In addition, the gateway 1888 may provide the WTRUs 1802a, 1802b, 1802c with access to the networks 1812, which may include other wired or wireless networks that are owned and/or operated by other service providers.

Although not shown in FIG. 18E, it will be appreciated that the RAN 1805 may be connected to other ASNs and the core network 1809 may be connected to other core networks.

The communication link between the RAN 1805 the other ASNs may be defined as an R4 reference point, which may include protocols for coordinating the mobility of the WTRUs 1802a, 1802b, 1802c between the RAN 1805 and the other ASNs. The communication link between the core network 1809 and the other core networks may be defined as an R5 reference, which may include protocols for facilitating interworking between home core networks and visited core networks.

The processes and instrumentalities described herein may apply in any combination, may apply to other wireless technology, and for other services (e.g., not limited for proximity services).

A WTRU may refer to an identity of the physical device, or to the user's identity such as subscription related identities, e.g., MSISDN, SIP URI, etc. WTRU may refer to application-based identities, e.g., user names that may be used per application.

The processes described above may be implemented in a computer program, software, and/or firmware incorporated in a computer-readable medium for execution by a computer and/or processor. Examples of computer-readable media include, but are not limited to, electronic signals (transmitted over wired and/or wireless connections) and/or computer-readable storage media. Examples of computer-readable storage media include, but are not limited to, a read only memory (ROM), a random access memory (RAM), a register, cache memory, semiconductor memory devices, magnetic media such as, but not limited to, internal hard disks and removable disks, magneto-optical media, and/or optical media such as CD-ROM disks, and/or digital versatile disks (DVDs). A processor in association with software may be used to implement a radio frequency transceiver for use in a WTRU, UE, terminal, base station, RNC, and/or any host computer.

What is claimed is:

1. A method for providing augmented reality (AR) to a user, comprising:
    estimating a gaze point of the user to define a first region of interest (ROI);
    adaptively adjusting the size of the first ROI based upon one or more of a gaze focused for a time on a portion of the first ROI exceeding a threshold or a number of objects of interest in the first ROI exceeding a threshold, wherein the adjusted ROI contains one or more physical objects currently in proximity to the user;
    extracting images from the adjusted ROI and creating a set of descriptors which describe the one or more physical objects without input from the user;
    estimating an emotional state of the user;
    determining a subset of descriptors by comparing the set of descriptors to the estimated emotional state of the user and giving greater weight to descriptors associated with an emotional state closest to the estimated emotional state of the user, wherein representative emotional states are mapped to descriptors of objects, such that objects consistent with the estimated emotional state of the user are prioritized;
    without further input from the user, searching for information regarding the one or more physical objects in the adjusted ROI using the subset of descriptors;
    retrieving the searched information prioritized by the subset of descriptors; and
    displaying the retrieved information.

2. The method of claim 1, further comprising estimating a second emotional state of the user upon viewing the retrieved information prioritized by the subset of descriptors regarding the one or more physical objects.

3. The method of claim 2, further comprising revising the subset of descriptors if the second emotional state of the user is a negative emotional state.

4. The method of claim 1, wherein the set of descriptors specify features of the one or more physical objects.

5. The method of claim 1, wherein the set of descriptors identify the one or more physical objects.

6. The method of claim 1, wherein the subset of descriptors is included in a retrieval request to a server.

7. The method of claim 1, wherein the subset of descriptors is used for a local search.

8. The method of claim 1, wherein the emotional state of the user is determined by estimating a point for the emotional state on a valence/arousal chart.

9. The method of claim 1, further comprising using one or more of voice recognition of an emotion of the user, facial recognition of an emotion of the user, and/or electroencephalographic (EEG) data of the user, to determine the emotional state of the user.

10. The method of claim 1, wherein the information regarding one or more physical objects in the adjusted ROI received from a server is less than the total information available for the one or more physical objects in the adjusted ROI.

11. A wireless transmit/receive unit (WTRU) for providing augmented reality (AR) to a user, comprising:
    a power source;
    a display/touchpad;
    a global positioning system (GPS) chipset;
    a camera;
    a memory; and
    a processor to execute instructions from the memory, the processor configured to:
        estimate a gaze point of the user to define a region of interest (ROI), the ROI being determined by a gaze of the user being focused for a time exceeding a threshold, wherein the ROI contains one or more physical objects currently in proximity to the user;
        extract images from the ROI and create a set of descriptors which describe the one or more physical objects;
        estimate an emotional state of the user, wherein the emotional state of the user is that the user is tired, alert, or hungry;
        determine a subset of descriptors by comparing the set of descriptors to the estimated emotional state of the user and giving greater weight to descriptors associated with an emotional state closest to the estimated emotional state of the user, wherein representative emotional states are mapped to descriptors of objects, such that objects consistent with the estimated emotional state of the user are prioritized;
        without further input from the user, search for information regarding the one or more physical objects in the ROI using the subset of descriptors;
        retrieve the searched information prioritized by the subset of descriptors; and
        display the retrieved information.

12. The WTRU of claim 11, wherein the processor configured to estimate a second emotional state of the user upon viewing the retrieved information prioritized by the subset of descriptors regarding the one or more physical objects, and to revise the subset of descriptors if the second emotional state of the user is a negative emotional state.

13. The WTRU of claim 11, wherein the set of descriptors specify features of the one or more physical objects.

14. The WTRU of claim 11, wherein the set of descriptors identify the one or more physical objects.

15. The WTRU of claim 11, wherein the subset of descriptors is included in a retrieval request to a server.

16. The WTRU of claim 11, wherein the subset of descriptors is used for a local search.

17. The WTRU of claim 11, wherein the emotional state of the user is determined by estimating a point for the emotional state on a valence/arousal chart.

18. The WTRU of claim 11, wherein the processor configured to use one or more of voice recognition of an emotion of the user, facial recognition of an emotion of the user, and/or electroencephalographic (EEG) data of the user, to determine the emotional state of the user.

19. A method for providing augmented reality (AR) to a user, comprising:
   estimating a gaze point of the user to define a region of interest (ROI), the ROI being determined by a gaze of the user being focused for a time exceeding a threshold, wherein the ROI contains one or more physical objects currently in proximity to the user;
   extracting images from the ROI and creating a set of descriptors which describe the one or more physical objects;
   estimating an emotional state of the user;
   determining a subset of descriptors by comparing the set of descriptors to the estimated emotional state of the user and giving greater weight to descriptors associated with an emotional state closest to the estimated emotional state of the user, wherein representative emotional states are mapped to descriptors of objects, such that objects consistent with the estimated emotional state of the user are prioritized;
   without further input from the user, searching for information regarding the one or more physical objects in the ROI using the subset of descriptors and retrieving the searched information;
   displaying the retrieved information prioritized by the subset of descriptors regarding the one or more physical objects; and
   thereafter, estimating a second emotional state of the user upon viewing the retrieved information prioritized by the subset of descriptors regarding the one or more physical objects.

20. A wireless transmit/receive unit (WTRU) having a memory and a processor to execute instructions from the memory, which, when executed, cause the WTRU to carry out the method of claim 19.

21. A method for providing augmented reality (AR) to a user with a WTRU having a power source, a display/touchpad, a global positioning system (GPS) chipset, a camera, a memory, and a processor to execute instructions from the memory, the method comprising:
   estimating a gaze point of the user to define a region of interest (ROI), the ROI being determined by a gaze of the user being focused for a time exceeding a threshold, wherein the ROI contains one or more physical objects currently in proximity to the user;
   extracting images from the ROI and creating a set of descriptors which describe the one or more physical objects;
   estimating an emotional state of the user, wherein the emotional state of the user is that the user is tired, alert, or hungry;
   determining a subset of descriptors by comparing the set of descriptors to the estimated emotional state of the user and giving greater weight to descriptors associated with an emotional state closest to the estimated emotional state of the user, wherein representative emotional states are mapped to descriptors of objects, such that objects consistent with the estimated emotional state of the user are prioritized;
   without further input from the user, searching for information regarding the one or more physical objects in the ROI using the subset of descriptors;
   retrieving the searched information prioritized by the subset of descriptors; and
   displaying the retrieved information.

* * * * *